US007666205B2

(12) United States Patent
Weikel et al.

(10) Patent No.: US 7,666,205 B2
(45) Date of Patent: Feb. 23, 2010

(54) INFLATABLE DEVICE AND METHOD FOR REDUCING FRACTURES IN BONE AND IN TREATING THE SPINE

(75) Inventors: Stuart Weikel, Drexel Hill, PA (US); David C. Paul, Phoenixville, PA (US)

(73) Assignee: Synthes USA, LLC, West Chester, PA (US)

( * ) Notice: Subject to any disclaimer, the term of this patent is extended or adjusted under 35 U.S.C. 154(b) by 721 days.

(21) Appl. No.: 10/636,549

(22) Filed: Aug. 8, 2003

(65) Prior Publication Data
US 2004/0098015 A1    May 20, 2004

Related U.S. Application Data

(63) Continuation of application No. 09/908,899, filed on Jul. 20, 2001, now Pat. No. 6,632,235.

(60) Provisional application No. 60/284,510, filed on Apr. 19, 2001.

(51) Int. Cl.
*A61M 29/00* (2006.01)
(52) U.S. Cl. .................................... 606/192; 623/23.19
(58) Field of Classification Search ................... 606/60, 606/94, 192, 61, 72, 76, 86, 191, 92, 194, 606/198; 623/17, 23.19, 23.2; 604/103.01
See application file for complete search history.

(56) References Cited

U.S. PATENT DOCUMENTS 2,381,050 A    8/1945    Hardinge

| 2,426,535 A | 8/1947 | Turkel ............................. 128/2 |
| 3,648,294 A | 3/1972 | Shahrestani ......................... 3/1 |
| 3,701,703 A | 10/1972 | Zimmer et al. |
| 3,741,204 A | 6/1973 | Thiele ...................... 128/92 R |

(Continued)

FOREIGN PATENT DOCUMENTS

DE    198 11 264 A1    9/1999

(Continued)

OTHER PUBLICATIONS

M. Pavlova et al., "Biocompatible and biodegradable polyurethane polymers," Biomaterials 14(13):1024-1029, 1993.

(Continued)

*Primary Examiner*—Anhtuan T Nguyen
*Assistant Examiner*—Tuan V Nguyen
(74) *Attorney, Agent, or Firm*—Stroock & Stroock & Lavan LLP

(57) ABSTRACT

The present invention is directed to an inflatable device for use in restoring the anatomy of diseased or fractured bone. The inflatable device may be a balloon of varied size or shape to conform to the bone to be treated and may be deployed in any type of bone where collapsed fractures of cortical bone may be treated by restoring the bone from its inner surface. Once the bone has been sufficiently restored the balloons may be deflated and removed, or may remain inside the bone. The balloon may have multiple layers to provide desired surface characteristics, resistance to puncture and tearing, or other beneficial properties, as appropriate for the particular application of the device.

32 Claims, 26 Drawing Sheets

U.S. PATENT DOCUMENTS

| | | | |
|---|---|---|---|
| 3,800,788 A | 4/1974 | White | 128/83 |
| 3,866,248 A | 2/1975 | Kummer | 3/1 |
| 3,867,728 A | 2/1975 | Stubstad et al. | 3/1 |
| 3,875,595 A | 4/1975 | Froning | 3/1 |
| 4,018,230 A | 4/1977 | Ochiai et al. | 128/344 |
| 4,055,029 A | 10/1977 | Kalbow et al. | |
| 4,200,939 A | 5/1980 | Oser | 3/1.9 |
| 4,213,461 A | 7/1980 | Pevsner | 128/348 |
| 4,274,163 A | 6/1981 | Malcom et al. | 3/1.91 |
| 4,313,434 A | 2/1982 | Segal | 128/92 BC |
| 4,327,736 A | 5/1982 | Inoue | 128/349 B |
| 4,369,772 A | 1/1983 | Miller | 128/92 |
| 4,399,814 A | 8/1983 | Pratt, Jr. et al. | 128/92 C |
| 4,448,195 A | 5/1984 | LeVeen et al. | 128/344 |
| 4,462,394 A | 7/1984 | Jacobs | 128/92 C |
| 4,466,435 A | 8/1984 | Murray | 128/303 R |
| 4,467,479 A | 8/1984 | Brody | 3/1.91 |
| 4,488,549 A | 12/1984 | Lee et al. | 128/303 R |
| 4,498,473 A | 2/1985 | Gereg | 128/207.15 |
| 4,562,598 A | 1/1986 | Kranz | 623/18 |
| 4,572,186 A | 2/1986 | Gould et al. | 128/341 |
| 4,595,006 A | 6/1986 | Burke et al. | 128/303 R |
| 4,627,434 A | 12/1986 | Murray | 128/303 R |
| 4,637,396 A | 1/1987 | Cook | 128/344 |
| 4,653,489 A | 3/1987 | Tronzo | 128/92 YV |
| 4,686,973 A | 8/1987 | Frisch | 129/92 YZ |
| 4,697,584 A | 10/1987 | Haynes | 128/92 VQ |
| 4,702,252 A | 10/1987 | Brooks et al. | 128/344 |
| 4,706,670 A | 11/1987 | Anderson et al. | 128/344 |
| 4,719,918 A | 1/1988 | Bonomo et al. | 123/344 |
| 4,760,844 A | 8/1988 | Kyle | 128/92 YQ |
| 4,772,287 A | 9/1988 | Ray et al. | 623/17 |
| 4,801,263 A | 1/1989 | Clark | 433/90 |
| 4,820,349 A | 4/1989 | Saab | 128/344 |
| 4,888,022 A | 12/1989 | Huebsch | 623/22 |
| 4,888,024 A | 12/1989 | Powlan | 623/23 |
| 4,892,550 A | 1/1990 | Huebsch | 623/22 |
| 4,896,662 A | 1/1990 | Noble | 606/94 |
| 4,904,260 A | 2/1990 | Ray et al. | 623/17 |
| 4,932,969 A | 6/1990 | Frey et al. | 623/17 |
| 4,932,975 A | 6/1990 | Main et al. | 623/17 |
| 4,941,877 A | 7/1990 | Montano, Jr. | 604/96 |
| 4,969,888 A | 11/1990 | Scholten et al. | 606/94 |
| 5,002,576 A | 3/1991 | Fuhrmann et al. | 623/17 |
| 5,021,241 A | 6/1991 | Yamahira et al. | 424/426 |
| 5,041,114 A | 8/1991 | Chapman et al. | |
| 5,059,193 A | 10/1991 | Kuslich | |
| 5,071,435 A | 12/1991 | Fuchs et al. | 623/16 |
| 5,087,244 A | 2/1992 | Wolinsky et al. | 604/509 |
| 5,102,413 A | 4/1992 | Poddar | 606/62 |
| 5,108,404 A | 4/1992 | Scholten et al. | 606/94 |
| 5,108,438 A | 4/1992 | Stone | 623/17 |
| 5,112,304 A | 5/1992 | Barlow et al. | 604/96 |
| 5,120,316 A * | 6/1992 | Morales et al. | 604/148 |
| 5,147,366 A | 9/1992 | Arroyo et al. | 606/94 |
| 5,163,949 A | 11/1992 | Bonutti | 606/192 |
| 5,171,280 A | 12/1992 | Baumgartner | 623/17 |
| 5,171,297 A | 12/1992 | Barlow et al. | 604/96 |
| 5,176,683 A | 1/1993 | Kimsey et al. | 606/86 |
| 5,192,296 A | 3/1993 | Bhate et al. | 606/194 |
| 5,192,326 A * | 3/1993 | Bao et al. | 623/17.12 |
| 5,201,706 A | 4/1993 | Noguchi et al. | 604/96 |
| 5,209,723 A | 5/1993 | Twardowski et al. | 604/43 |
| 5,213,580 A | 5/1993 | Slepian et al. | 623/1 |
| 5,246,421 A | 9/1993 | Saab | 604/96 |
| 5,264,260 A | 11/1993 | Saab | 428/35.5 |
| 5,270,086 A | 12/1993 | Hamlin | 428/35.2 |
| 5,295,994 A | 3/1994 | Bonutti | 606/192 |
| 5,300,025 A | 4/1994 | Wantink | 604/96 |
| 5,303,718 A | 4/1994 | Krajicek | 128/897 |
| 5,324,261 A * | 6/1994 | Amundson et al. | 604/103.02 |
| 5,330,429 A | 7/1994 | Noguchi et al. | 604/96 |
| 5,331,975 A | 7/1994 | Bonutti | 128/898 |
| 5,336,178 A | 8/1994 | Kaplan et al. | 604/509 |
| 5,337,734 A | 8/1994 | Saab | 128/4 |
| 5,338,295 A | 8/1994 | Cornelius et al. | 604/96 |
| 5,338,299 A | 8/1994 | Barlow | 604/96 |
| 5,342,301 A | 8/1994 | Saab | 604/96 |
| 5,344,459 A | 9/1994 | Swartz | 623/18 |
| 5,358,486 A | 10/1994 | Saab | 604/96 |
| 5,364,357 A | 11/1994 | Aase | 604/96 |
| 5,370,614 A | 12/1994 | Amundson et al. | 604/96 |
| 5,383,929 A | 1/1995 | Ledergerber | 623/8 |
| 5,390,683 A | 2/1995 | Pisharodi | |
| 5,411,477 A | 5/1995 | Saab | 604/96 |
| 5,423,824 A | 6/1995 | Akerfeldt et al. | 606/80 |
| 5,423,850 A | 6/1995 | Berger | 606/192 |
| 5,443,496 A | 8/1995 | Schwartz et al. | |
| 5,443,781 A | 8/1995 | Saab | 264/291 |
| 5,456,665 A | 10/1995 | Postell et al. | 604/96 |
| 5,460,608 A | 10/1995 | Lodin et al. | 604/96 |
| 5,466,222 A | 11/1995 | Ressemann et al. | 604/96 |
| 5,466,262 A | 11/1995 | Saffran | 623/16 |
| 5,468,245 A | 11/1995 | Vargas, III | 606/94 |
| 5,480,400 A | 1/1996 | Berger | 606/60 |
| 5,492,532 A | 2/1996 | Ryan et al. | 604/96 |
| 5,499,973 A | 3/1996 | Saab | 604/96 |
| 5,514,153 A | 5/1996 | Bonutti | 606/190 |
| 5,533,987 A | 7/1996 | Pray et al. | 604/280 |
| 5,549,679 A | 8/1996 | Kuslich | 623/17 |
| 5,550,172 A | 8/1996 | Regula et al. | 523/118 |
| 5,556,382 A | 9/1996 | Adams | 604/96 |
| 5,562,736 A | 10/1996 | Ray et al. | 623/17 |
| 5,569,195 A | 10/1996 | Saab | 604/96 |
| 5,569,219 A | 10/1996 | Hakki et al. | 604/282 |
| 5,571,189 A * | 11/1996 | Kuslich | 623/17.12 |
| 5,591,234 A | 1/1997 | Kirsch | 623/16 |
| 5,599,301 A | 2/1997 | Jacobs et al. | |
| 5,601,593 A | 2/1997 | Freitag | |
| 5,624,392 A | 4/1997 | Saab | 604/43 |
| 5,634,936 A * | 6/1997 | Linden et al. | 606/213 |
| 5,645,597 A | 7/1997 | Krapiva | 623/17 |
| 5,647,848 A | 7/1997 | Jørgensen | 604/96 |
| 5,653,689 A | 8/1997 | Buelna et al. | 604/96 |
| 5,653,760 A | 8/1997 | Saffran | 623/11 |
| 5,658,310 A | 8/1997 | Berger | 606/192 |
| 5,660,225 A | 8/1997 | Saffran | 623/16 |
| 5,665,121 A | 9/1997 | Gie et al. | 623/16 |
| 5,674,295 A | 10/1997 | Ray et al. | 623/17 |
| 5,693,100 A | 12/1997 | Pisharodi | |
| 5,697,932 A | 12/1997 | Smith et al. | 606/80 |
| 5,702,410 A | 12/1997 | Klunder et al. | 606/194 |
| 5,707,390 A | 1/1998 | Bonutti | |
| 5,716,416 A | 2/1998 | Lin | 623/17 |
| 5,718,707 A | 2/1998 | Mikhail | 606/94 |
| 5,728,063 A | 3/1998 | Preissman et al. | 604/96 |
| 5,735,902 A | 4/1998 | Li et al. | 623/18 |
| 5,755,690 A | 5/1998 | Saab | 604/96 |
| 5,755,797 A | 5/1998 | Baumgartner | 623/17 |
| 5,759,173 A | 6/1998 | Preissman et al. | 604/96 |
| 5,759,191 A | 6/1998 | Barbere | |
| 5,772,681 A | 6/1998 | Leoni | 606/192 |
| 5,788,703 A | 8/1998 | Mittelmeier et al. | 606/94 |
| 5,800,439 A | 9/1998 | Clyburn | 606/94 |
| 5,810,826 A | 9/1998 | Akerfeldt et al. | 606/80 |
| 5,820,613 A | 10/1998 | Van Werven-Franssen et al. | 604/282 |
| 5,824,087 A | 10/1998 | Aspden et al. | 623/16 |
| 5,824,088 A | 10/1998 | Kirsch | 623/16 |
| 5,824,093 A | 10/1998 | Ray et al. | 623/17 |
| 5,827,289 A | 10/1998 | Reiley et al. | 606/86 |
| 5,847,046 A | 12/1998 | Jiang et al. | 524/42 |
| 5,849,014 A | 12/1998 | Mastrorio et al. | 606/94 |
| 5,868,779 A | 2/1999 | Ruiz | 606/194 |

| Patent Number | Date | Inventor | Class |
|---|---|---|---|
| 5,888,220 A | 3/1999 | Felt et al. | 623/17 |
| 5,891,090 A | 4/1999 | Thornton | 604/102 |
| 5,893,850 A | 4/1999 | Cachia | |
| 5,902,268 A | 5/1999 | Saab | 604/96 |
| 5,906,606 A | 5/1999 | Chee et al. | 604/527 |
| 5,925,051 A | 7/1999 | Mikhail | 606/94 |
| 5,935,169 A | 8/1999 | Chan | 623/16 |
| 5,954,728 A | 9/1999 | Heller et al. | 606/92 |
| 5,961,490 A | 10/1999 | Adams | 604/96 |
| 5,972,015 A | 10/1999 | Scribner et al. | 606/192 |
| 5,976,186 A | 11/1999 | Bao et al. | 623/17 |
| 5,984,926 A | 11/1999 | Jones | 606/72 |
| 5,997,582 A | 12/1999 | Weiss | 623/23 |
| 6,004,289 A | 12/1999 | Saab | 604/96 |
| 6,017,305 A | 1/2000 | Bonutti | 600/207 |
| 6,022,369 A * | 2/2000 | Jacobsen et al. | 606/191 |
| 6,022,376 A | 2/2000 | Assell et al. | 623/17 |
| 6,048,346 A | 4/2000 | Reiley et al. | 606/92 |
| 6,063,112 A * | 5/2000 | Sgro | 623/1.12 |
| 6,066,154 A * | 5/2000 | Reiley et al. | 606/192 |
| 6,096,038 A | 8/2000 | Michelson | |
| 6,110,210 A | 8/2000 | Norton et al. | 623/17.16 |
| 6,110,211 A | 8/2000 | Weiss | 623/23.11 |
| 6,113,603 A | 9/2000 | Medoff | 606/69 |
| 6,113,639 A | 9/2000 | Ray et al. | 623/17.16 |
| 6,127,597 A | 10/2000 | Beyar et al. | 623/16 |
| 6,132,465 A | 10/2000 | Ray et al. | 623/17.16 |
| 6,143,013 A | 11/2000 | Samson et al. | 606/192 |
| 6,179,842 B1 | 1/2001 | Spotorno et al. | 606/95 |
| 6,179,856 B1 | 1/2001 | Barbere | |
| 6,186,978 B1 | 2/2001 | Samson et al. | 604/96.01 |
| 6,187,043 B1 | 2/2001 | Ledergerber | 623/8 |
| 6,187,048 B1 | 2/2001 | Milner et al. | 623/17.12 |
| 6,193,686 B1 | 2/2001 | Estrada et al. | 604/103.09 |
| D439,980 S | 4/2001 | Reiley et al. | D24/147 |
| 6,235,043 B1 | 5/2001 | Reiley et al. | 606/192 |
| 6,241,734 B1 | 6/2001 | Scribner et al. | 606/93 |
| 6,248,110 B1 | 6/2001 | Reiley et al. | 606/93 |
| 6,248,131 B1 | 6/2001 | Felt et al. | 623/17.12 |
| 6,280,456 B1 | 8/2001 | Scribner et al. | 606/192 |
| 6,287,313 B1 | 9/2001 | Sasso | 606/96 |
| D449,691 S | 10/2001 | Reiley et al. | D24/147 |
| 6,306,177 B1 | 10/2001 | Felt et al. | |
| 6,332,894 B1 | 12/2001 | Stalcup et al. | 623/17.11 |
| 6,336,930 B1 | 1/2002 | Stalcup et al. | 606/69 |
| 6,355,013 B1 * | 3/2002 | van Muiden | 604/96.01 |
| 6,356,782 B1 | 3/2002 | Sirimanne et al. | 600/431 |
| 6,375,659 B1 | 4/2002 | Erbe et al. | 606/94 |
| 6,395,007 B1 | 5/2002 | Bhatnagar et al. | 606/94 |
| 6,395,032 B1 | 5/2002 | Gauchet | |
| 6,402,750 B1 | 6/2002 | Atkinson et al. | 606/61 |
| 6,416,776 B1 | 7/2002 | Shamie | 424/423 |
| 6,423,083 B2 | 7/2002 | Reiley et al. | 606/192 |
| 6,425,923 B1 | 7/2002 | Stalcup et al. | 623/23.58 |
| 6,428,576 B1 | 8/2002 | Haldimann | 623/17.16 |
| 6,440,138 B1 | 8/2002 | Reiley et al. | 606/79 |
| 6,443,988 B2 | 9/2002 | Felt et al. | 623/17.12 |
| 6,447,515 B1 | 9/2002 | Meldrum | 606/63 |
| 6,468,279 B1 | 10/2002 | Reo | 606/79 |
| 6,478,800 B1 | 11/2002 | Fraser et al. | |
| 6,558,390 B2 | 5/2003 | Cragg | |
| 6,613,054 B2 | 9/2003 | Scribner et al. | |
| 6,620,162 B2 | 9/2003 | Kuslich et al. | |
| 6,632,235 B2 | 10/2003 | Weikel et al. | |
| 6,663,647 B2 | 12/2003 | Reiley et al. | |
| 6,679,886 B2 | 1/2004 | Weikel et al. | |
| 6,706,069 B2 | 3/2004 | Berger | |
| 6,716,216 B1 | 4/2004 | Boucher et al. | |
| 6,719,761 B1 | 4/2004 | Reiley et al. | |
| 6,726,691 B2 | 4/2004 | Osorio et al. | |
| 6,733,532 B1 | 5/2004 | Gauchet et al. | |
| 6,740,093 B2 | 5/2004 | Hochschuler et al. | |
| 6,863,672 B2 | 3/2005 | Reiley et al. | |
| 6,899,719 B2 | 5/2005 | Reiley et al. | |
| 6,981,981 B2 | 1/2006 | Reiley et al. | |
| 7,025,771 B2 | 4/2006 | Kuslich et al. | |
| 7,044,954 B2 | 5/2006 | Reiley et al. | |
| 7,097,648 B1 | 8/2006 | Globerman et al. | |
| 7,153,307 B2 | 12/2006 | Scribner et al. | |
| 7,166,121 B2 | 1/2007 | Reiley et al. | |
| 7,226,481 B2 | 6/2007 | Kuslich | |
| 7,241,303 B2 | 7/2007 | Reiss et al. | |
| 7,261,720 B2 | 8/2007 | Stevens et al. | |
| 2001/0004710 A1 | 6/2001 | Felt et al. | 623/17.12 |
| 2001/0011174 A1 | 8/2001 | Reiley et al. | 606/86 |
| 2001/0023371 A1 | 9/2001 | Bonutti | 623/23.48 |
| 2001/0032019 A1 | 10/2001 | Van Dyke et al. | 623/17.12 |
| 2001/0034527 A1 | 10/2001 | Scribner et al. | 606/93 |
| 2001/0041896 A1 | 11/2001 | Reiley et al. | 606/86 |
| 2001/0044626 A1 | 11/2001 | Reiley et al. | 606/53 |
| 2001/0049527 A1 | 12/2001 | Cragg | 606/61 |
| 2001/0049531 A1 | 12/2001 | Reiley et al. | 606/93 |
| 2002/0013600 A1 | 1/2002 | Scribner et al. | 606/192 |
| 2002/0022856 A1 | 2/2002 | Johnson et al. | 606/185 |
| 2002/0032444 A1 | 3/2002 | Mische | 606/63 |
| 2002/0049448 A1 | 4/2002 | Sand et al. | 606/92 |
| 2002/0058947 A1 * | 5/2002 | Hochschuler et al. | 606/94 |
| 2002/0068974 A1 | 6/2002 | Kuslich et al. | 623/17.11 |
| 2002/0068975 A1 | 6/2002 | Teitelbaum et al. | 623/17.11 |
| 2002/0077701 A1 | 6/2002 | Kuslich | 623/17.12 |
| 2002/0082600 A1 | 6/2002 | Shaolian et al. | 606/61 |
| 2002/0082605 A1 | 6/2002 | Reiley et al. | 606/93 |
| 2002/0082608 A1 | 6/2002 | Reiley et al. | 606/105 |
| 2002/0099384 A1 | 7/2002 | Scribner et al. | 606/92 |
| 2002/0099385 A1 | 7/2002 | Ralph et al. | 606/92 |
| 2002/0123750 A1 | 9/2002 | Eisermann et al. | 606/69 |
| 2002/0161373 A1 | 10/2002 | Osorio et al. | 606/86 |
| 2002/0169471 A1 | 11/2002 | Ferdinand | 606/185 |
| 2002/0188299 A1 | 12/2002 | Reiley et al. | 606/79 |
| 2003/0220649 A1 | 11/2003 | Bao et al. | |
| 2004/0073308 A1 | 4/2004 | Kuslich et al. | |
| 2004/0097930 A1 | 5/2004 | Justis et al. | |
| 2004/0102774 A1 | 5/2004 | Trieu | |
| 2004/0167625 A1 | 8/2004 | Beyar et al. | |
| 2004/0210297 A1 | 10/2004 | Lin et al. | |
| 2004/0215343 A1 | 10/2004 | Hochschuler et al. | |
| 2004/0215344 A1 | 10/2004 | Hochschuler et al. | |
| 2004/0220615 A1 | 11/2004 | Lin et al. | |
| 2005/0070911 A1 | 3/2005 | Carrison et al. | |
| 2005/0143827 A1 | 6/2005 | Globerman et al. | |
| 2005/0234498 A1 | 10/2005 | Gronemeyer et al. | |
| 2006/0079905 A1 | 4/2006 | Beyar et al. | |
| 2006/0100706 A1 | 5/2006 | Shadduck et al. | |
| 2006/0190083 A1 | 8/2006 | Arnin et al. | |
| 2006/0271061 A1 | 11/2006 | Beyar et al. | |
| 2006/0293750 A1 | 12/2006 | Sherman et al. | |
| 2007/0055266 A1 | 3/2007 | Osorio et al. | |
| 2007/0055267 A1 | 3/2007 | Osorio et al. | |
| 2007/0055280 A1 | 3/2007 | Osorio et al. | |
| 2007/0055284 A1 | 3/2007 | Osorio et al. | |
| 2007/0055285 A1 | 3/2007 | Osorio et al. | |
| 2007/0282443 A1 | 12/2007 | Globerman et al. | |

FOREIGN PATENT DOCUMENTS

| | | |
|---|---|---|
| EP | 0 493 789 | 12/1991 |
| GB | 2 358 589 A | 8/2001 |
| JP | 02-279165 | 11/1990 |
| JP | 4-303444 | 10/1992 |
| JP | 8-98850 | 4/1996 |
| JP | 11-9618 | 1/1999 |
| WO | WO 93/16664 | 9/1993 |
| WO | WO 96/39970 | 12/1996 |
| WO | WO 97/26847 | 7/1997 |
| WO | WO 98/05377 | 2/1998 |
| WO | WO 98/20939 | 5/1998 |

| | | |
|---|---|---|
| WO | WO 98/56301 | 12/1998 |
| WO | WO 99/08616 | 2/1999 |
| WO | WO 99/29246 | 6/1999 |
| WO | WO 99/37212 | 7/1999 |
| WO | WO 99/51149 | 10/1999 |
| WO | WO 99/62416 | 12/1999 |
| WO | WO 00/09024 | 2/2000 |
| WO | WO 01/28439 A1 | 4/2001 |
| WO | WO 01/34026 A1 | 5/2001 |
| WO | WO 01/76514 | 10/2001 |
| WO | WO 01/76514 A2 | 10/2001 |
| WO | WO 02/00143 A1 | 1/2002 |
| WO | WO 02/17801 A2 | 3/2002 |
| WO | WO 02/30338 A1 | 4/2002 |
| WO | WO 02/43628 | 6/2002 |
| WO | WO 03/007853 | 1/2003 |
| WO | WO 2005/048856 | 6/2005 |

OTHER PUBLICATIONS

M. Szycher, "Biostability of Polyurethane Elastomers: A Critical Review," *Journal of Biomaterials Applications*, 3:297-402, 1988.

A. Coury et al., "Factors and Interactions Affecting the Performance of Polyurethane Elastomers in Medical Devices*," *Journal of Biomaterials Applications*, 3:130-179, 1988.

Mary E. Jensen et al., "Percutaneous Polymethylmethacrylate Vertebroplasty in the Treatment of Osteoporotic Vertebral Body Compression Fractures: Technical Aspects," *AJNR Am J. Neuroradiol*. 18: 1897-1904, Nov. 1997.

Afshin Gangi et al., "Percutaneous Vertebroplasty Guided by a Combination of CT and Fluoroscopy," AJNR 15:83-86, Jan. 1994.

Mark A. Saab, "Applications of High-Pressure Balloons in the Medical Device Industry," *Medical Device & Diagnostic Industry*, Sep. 2000, pp. 86-97.

"The Heart Center One of First in U.S. to Use New Angioplasty Device," http://216.117.145.213/news/0800/cuttingballoon.html.

PLIF Spacer Instruments Technique Guide, Synthes Spine, Apr. 1999.

Szycher, M., "Biostability of Polyurethane Elastomers: A Critical Review", J. Biomaterials Applications, vol. 3 (1988), pp. 297-402.

Coury, A. et al., "Factors and Interactions Affecting the Performance of Polyurethane Elastomers in Medical Devices", J. Biomaterials Applications, vol. 3 (1988), pp. 130-179.

Pavlova, M. et al., "Biocompatible and Biodegradable Polyurethane Polymers", Biomaterials 14(13) (1993), pp. 1024-1029.

"Kyphoplasty Surgical Technique Guide," May 12, 1999, pp. 1-33.

Jensen, Mary E., et al., "Percutaneous Polymethylmethacrylate Vertebroplasty in the Treatment of Osteoporotic Vertebral Body Compression Fractures: Technical Aspects"., AJNR: 18, Nov. 1997.

Gangi, Afshin, et al., "Percutaneous Vertebroplasty Guided by a Combination of CT and Fluoroscopy"., AJNR 15:83-86, Jan. 1994.

Cotten, Anne., MD., et al. "Percutaneous Vertebroplasty for Osteolytic Metastases and Myeloma: Effects of the Percentage of Lesion Filling and the Leakage of Methyl Methacrylate at Clinical Follow-up"., Radiology 1996; 200:525-530.

Cotten, Anne, et al., "Preoperative Percutaneous Injection of Methyl Methacrylate and N-Butyl Cyanoacrylate in Vertebral Hemangiomas"; AJNR 17:137-142 (1996).

Maciunas, Robert J., MD., "Endovascular Neurological Intervention"; American Association of Neurological Surgeons; 153-158.

Japanese Patent Office; Final Rejection dated Jun. 30, 2009.

* cited by examiner

INFLATABLE DEVICE AND METHOD FOR REDUCING FRACTURES IN BONE AND IN TREATING THE SPINE

CROSS-REFERENCE TO RELATED APPLICATIONS

This application is a continuation of application Ser. No. 09/908,899, filed Jul. 20, 2001 now U.S. Pat. No. 6,632,235, which claims the benefit under 35 U.S.C. §119(e) of Provisional Application No. 60/284,510, filed Apr. 19, 2001. The entire content of these applications is expressly incorporated herein by reference thereto.

FIELD OF THE INVENTION

The present invention is directed to an inflatable device and method for use in orthopedic procedures to treat bone, and in particular to an improved device and method for reducing fractures in bone and treatment of the spine.

BACKGROUND OF THE INVENTION

Medical balloons are commonly known for dilating and unblocking arteries that feed the heart (percutaneous translumenal coronary angioplasty) and for arteries other than the coronary arteries (noncoronary percutaneous translumenal angioplasty). In angioplasty, the balloon is tightly wrapped around a catheter shaft to minimize its profile, and is inserted through the skin and into the narrowed section of the artery. The balloon is inflated, typically, by saline or a radiopaque solution, which is forced into the balloon through a syringe. Conversely, for retraction, a vacuum is pulled through the balloon to collapse it.

Medical balloons also have been used for the treatment of bone fractures. One such device is disclosed in U.S. Pat. No. 5,423,850 to Berger, which teaches a method and an assembly for setting a fractured tubular bone using a balloon catheter. The balloon is inserted far away from the fracture site through an incision in the bone, and guide wires are used to transport the uninflated balloon through the medullary canal and past the fracture site for deployment. The inflated balloon is held securely in place by the positive pressure applied to the intramedullary walls of the bone. Once the balloon is deployed, the attached catheter tube is tensioned with a calibrated force measuring device. The tightening of the catheter with the fixed balloon in place aligns the fracture and compresses the proximal and distal portions of the fractured bone together. The tensioned catheter is then secured to the bone at the insertion site with a screw or similar fixating device.

As one skilled in the related art would readily appreciate, there is a continuing need for new and innovative medical balloons and balloon catheters, and in particular a need for balloon catheter equipment directed toward the treatment of diseased and damaged bones. More specifically, there exists a need for a low profile, high-pressure, puncture and tear resistant medical balloon, that can be used to restore the natural anatomy of damaged cortical bone.

SUMMARY OF THE INVENTION

The present invention is directed to an inflatable device for use in restoring the anatomy of diseased or fractured bone such as for treatment of the spine. In one embodiment, the inflatable device is a balloon-tipped catheter. The catheter and/or balloon may be varied in size, shape, or configuration according to the desired application. The device may be deployed in any type of bone where collapsed fractures of cortical bone may be treated by restoring the bone from its inner surface. Examples of such bones include, without limitation, vertebral bodies, long bones, the distal radius, and the tibial plateau. Additionally, the inflatable device may also be adapted for use as a spinal prosthesis. For instance, a balloon of the present invention may be designed and configured to replace a vertebral disk, or may serve as a distraction instrument and implant for intervertebral fusion.

The invention is constructed in a manner specialized to restore the anatomy of a fractured bone which has sufficient normal cancellous volume to contain the device. The device is constructed for controlled deployment and reliability at pressures between about 40 to about 400 psi, more preferably at between about 200 to about 300 psi, and most preferably at about 250 psi. The present invention comprises a balloon catheter device in which the inflatable vessel comprises a puncture and tear resistant balloon.

In one embodiment, the inflatable device has a layer of puncture and tear resistant material. In another embodiment, the balloon has multiple layers or coatings of material. The layers or coatings may be applied to achieve a desired shape, feel, performance, or appearance. For instance, layers may be provided to achieve a desired texture, surface characteristic, or color. Examples of surface characteristics include a high or low friction surfaces, and regions of the device capable of providing enhanced gripping to help anchor the device or position it as it is inflated. The outer layer or coating of the inflatable device also may be either hydrophobic or hydrophillic, depending on the degree of "wetability" desired.

In another embodiment, the invention comprises a rigid catheter which allows for the placement and deployment of the balloon tipped catheter without internal structural reinforcement. This provides the catheter with surprising advantages, including improved surgical control over placement of the balloon tip and rotational control over the balloon during deployment.

The shape of the inflatable device and/or catheter may be curved, shaped or otherwise configured to allow for an easier approach to the bone cavity or to correspond to the portion of the bone which is to be restored. In one embodiment, an axial balloon is constructed with a uniform bulge and blunt distal end to allow the deployment of the balloon against the wall of the prepared bone cavity, and to facilitate uniform expansive pressure in the cavity when inflated. In another embodiment, an offset balloon of circular cross section is employed, while another embodiment uses an offset balloon with a non-circular cross section. In another embodiment, the balloon may be curved to correspond to the interior wall of the cortical bone. In yet another embodiment, a shape memory catheter is used to better position the inflatable device within right or left bones, or in the left or right side of bones that possess a sagittal plane of symmetry.

One embodiment uses a plurality of offset balloons on a single catheter. Deployment and deflation of the balloons can be varied according to the surgical procedure performed by the surgeon. In one embodiment, the plurality of balloons are deployed to restore the cortical bone. Then, one or more balloons is selectively deflated so that bone filler material may be injected into the region previously occupied by the balloon. Once the bone filler has sufficiently gelled or hardened in this region, the remaining balloon or balloons similarly may be deflated and the bone filled.

In one embodiment, the region occupied by the deployed balloon is filled with bone filler at the same time that the balloon is being deflated. Preferably, the rate at which the region is filled with bone filler material is approximately the same rate at which the balloon is deflated so that the volume of the treated region within the bone remains approximately the same.

In yet another embodiment, the cavity may be treated with a sealing material prior to or after deployment of the balloon. The use of a sealant may assist in reducing or preventing leakage of filler material from the cavity, or to prevent bone materials or body fluids from leaching into the cavity. Generally, sealants comprising fibrin or other suitable natural or synthetic constituents may be used for this purpose. The sealant materials may be delivered to the cavity walls by spray application, irrigation, flushing, topical application, or other suitable means, including applying sealant materials to the balloon exterior as a coating. The sealant, also, may be placed inside the treated area first, and then an inflatable device may be used to push the sealant outward toward the cavity walls.

Additionally, the bone cavity may be irrigated and/or aspirated. Irrigation media may comprise saline, water, antibiotic solution or other appropriate fluids to wash the bony interior and release debris. Aspiration of the bone cavity may be used to help clear the bone cavity of bony debris, fatty marrow, and blood products that may prevent adequate dispersal of filler material or that may constrict the cavity. Each of the steps of applying a sealant, irrigating and aspirating may be considered optional, and may be performed after inflation of the balloon, or before, or not at all.

The invention also relates to a method for reducing bone fractures comprising forming a cavity within a damaged bone, inserting the inflatable device into the cavity, inflating the device so that it restores collapsed or deteriorated portions of the cortical bone, preferably returning the bone approximately to its natural anatomy. In a preferred embodiment, a cavity is created in the portion of the bone in which the device is to be deployed and inflated. In one embodiment, the cavity is irrigated before the device is inserted into the bone in order to remove bone marrow and cancellous bone from the area where the device will be inflated. The inflatable device is inserted into the bone and positioned so that inflation of the balloon will assist in restoration of the cortical bone. Once the cortical bone has been sufficiently restored, the balloons may be deflated either in succession or altogether. Bone filler may be added to the region previously occupied by the balloon. Alternatively, the balloon or balloons may be deflated and bone filler injected simultaneously as described in the embodiments above.

In another embodiment, the inflatable device may remain inside the patient for an extended period after the surgical procedure is completed. In one embodiment, the inflatable device remains inside a treated bone. The inflatable device also may be adapted for disk replacement. An inflatable device for disk replacement may be designed to be biologically resorbable while leaving filler material in place or may remain indefinitely. The present invention may be further adapted for use as a distraction device and synthetic allograft spacer for intervertebral fusion.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

In the description that follows, any reference to either orientation or direction is intended primarily for the convenience of description and is not intended in any way to limit the scope of the present invention thereto.

Figure 1:
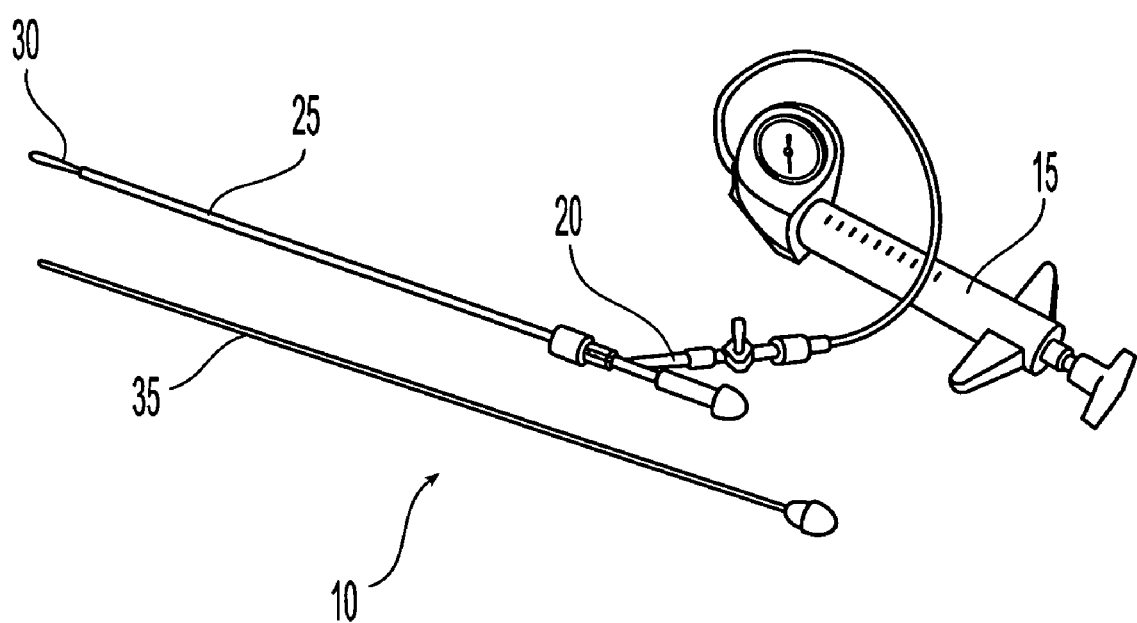
FIG. 1 shows a perspective view of a medical balloon catheter system according to the present invention.

FIG. 1 shows an apparatus 10 for use in reducing bone fractures according to the method of the present invention. The apparatus 10 comprises an inflation device 15, y-connector 20, catheter shaft 25, balloon 30, and hub shaft 35. As shown in FIG. 1, The balloon 10 is shown at the distal end of the catheter shaft 25, prior to deployment. The instruments illustrated in FIG. 1 are representative of the tools and other devices that may be used in conjunction with the balloon. These tools, however, may not always be required or may be replaced by different devices that perform similar, additional, or different functions. For example, one of ordinary skill in the art would appreciate that the y-connector 20 may be replaced by a wide variety of other suitable devices.

The balloon 30 may be used to treat any bone with an interior cavity sufficiently large enough to receive the balloon 30. Non-limiting examples of bones that are suitable candidates for anatomical restoration using the device and method of the present invention include vertebral bodies, the medullary canals of long bones, the calcaneus and the tibial plateau. The balloon 30 can be designed and adapted to accommodate particular bone anatomies and different cavity shapes, which may be made in these and other suitably large bones.

Additionally, the balloon may be designed and configured to be deployed and remain in the bone cavity for an extended period of time. For instance, the balloon may be inflated with natural or synthetic bone filler material or other suitable inflation fluid once the balloon is located within the bone cavity. Once filled, the balloon is allowed to remain within the bone for a prescribed period or perhaps indefinitely. The duration of time that the balloon remains within the bone may depend upon specific conditions in the treated bone or the particular objective sought by the treatment. For example, the balloon may remain within the cavity for less than a day, for several days, weeks, months or years, or even may remain within the bone permanently. As explained in greater detail below, the balloon may also be adapted to serve as a prosthetic device outside of a specific bone cavity, such as between two adjacent vertebrae.

In addition, the outer surface of the balloon may be treated with a coating or texture to help the balloon become more integral with the surrounding bone matter or to facilitate acceptance the balloon by the patient. The selection of balloon materials, coatings and textures also may help prevent rejection of the balloon by the body. The inner surface of the balloon likewise may be textured or coated to improve the performance of the balloon. For instance, the inner surface of the balloon may be textured to increase adhesion between the balloon wall and the material inside.

In yet another embodiment, the balloon may be designed to rupture, tear or otherwise open after the filler material injected inside the balloon has set up or sufficiently gelled, cured or solidified. The balloon may then be removed from the bone while leaving the filler material inside. This approach may result in a more controlled deployment of bone filler material to a treated area. It also may allow the bone filler material to be at least partially preformed before being released into the bone. This may be particularly beneficial where leakage of bone filler material out of damaged cortical bone may be a concern, although there may be other situations where this configuration would also be beneficial.

Alternatively, the balloon may be opened or ruptured in a manner that would permit the filler material to allow the inflation fluid to be released into the cavity. For instance, the opening of the balloon may be predetermined so that the flow of filler material travels in a desired direction. Moreover, the filler material may be held within the balloon until it partially sets so that, upon rupture of the balloon, the higher viscosity of the filler material limits the extent to which the filler material travels.

The balloon also may be designed and configured to release inflation fluid into the cavity in a more controlled fashion. For instance, the balloon catheter might be provided with a mechanism to initiate the rupture process in a highly controlled fashion. In one embodiment, predetermined seams in the balloon might fail immediately and rupture at a certain pressure. In another embodiment, the seams might fail only after prolonged exposure to a certain pressure, temperature, or material.

One skilled in the art would appreciate any number of ways to make the balloon open or rupture without departing from the spirit and scope of the present invention. For example, at least a portion of the balloon may be dissolved until the filler material is released into the bone cavity. In another example, the balloon may rupture and become harmlessly incorporated into the inflation fluid medium. In yet another example, the filler material may be designed to congeal when contacted to a chemical treatment applied to the surface of the balloon. In yet another embodiment, two balloons (or a single balloon having two chambers) may be designed and configured to release a combination of fluids that when mixed together react to form an inert filler material within the cavity. In another embodiment, different areas of the seam or balloon might be designed to rupture at different predetermined pressures or at different times.

Further, the balloon may be designed to be opened in any number of ways. For instance, a surgeon may lyse the balloon once the desired conditions of the bone filler material are reached. A balloon adapted to rupture and release inflation fluid into direct contact with a cavity also may be designed and configured to split along predetermined seams. The seams might run parallel to the longitudinal axis of the balloon and remain secured to the catheter at the proximal tip of the balloon, resembling a banana peel which has been opened. In another embodiment, the predetermined seams might consist of a single spiraling seam originating form the distal tip of the balloon and ending at the proximal tip of the balloon, resembling an orange peel which has been opened.

Other balloon adaptations may be provided to lyse the balloon in a controlled fashion. For instance, a balloon may be constructed with failure zones that are adapted so that structural failure under a triggering condition would occur preferentially in a localized area. For instance, a balloon might have a failure zone comprising a thinner membrane. In another example, the balloon might be designed to lack tensile reinforcing elements in a particular region. In yet another example, a region of the balloon might be comprised of a material that would fail due to a chemical reaction. For instance, the chemical reaction may be an oxidation or reduction reaction wherein the material might sacrificially neutralize a weak acid or base. In another example, the sacrificial region might comprise a pattern of pore like regions. This sacrificial region may comprise a specific pattern of pores that might form a latent perforation in the balloon membrane or may be randomly distributed in a localized area.

The ruptured balloon may then be removed from the bone cavity, leaving behind the deployed bone filler material. To facilitate removal of the ruptured balloon from the bone cavity, the balloon may be treated with special coating chemicals or substances or may be textured to prevent the balloon from sticking to the filler material or cavity walls. In one embodiment, the balloon might open at the distal end. This configuration may allow the balloon to be more readily removed from the bone cavity after the balloon has opened or ruptured.

Also, biologically resorbable balloons may be designed and configured according to the present invention. For instance, a deployed balloon comprising bio-resorbable polymers might be transformed by physiological conditions into substances which are non-harmful and biologically compatible or naturally occurring in the body. These substances may remain in the patient or be expelled from the body via metabolic activity. In one example, a balloon designed to restore the anatomy of a vertebral body would be placed within a prepared cavity inside the treated vertebra and inflated with a radio-opaque filler material. Immediately after inflation (or after the filler material has partially set), the balloon may be disengaged, separated, or detached from the catheter to remain within the bone. As the balloon resorbs new bone may replace the filler material. Alternatively, the filler material may be converted by biological activity into bone or simply remain in the bone.

As one skilled in the art would readily appreciate a deployed balloon may be designed for partial or complete resorption. For instance, a selectively resorbable balloon may be configured to produce a bio-inert implant, structure, or a configuration comprising a plurality of such entities. For example, a balloon may have a resorbable membrane component and a biologically inert structural reinforcing component. In another example, a balloon designed to be selectively resorbable might form a series of bio-inert segments. These bio-inert segments might provide structural containment, or a reinforcing interface at weakened portions of the cortical bone. The segments may also be designed to cooperate and beneficially dissipate post operative stresses generated at the interface between the restored cortical bone and filler material. The precise nature of the stress reduction may be adapted to a particular anatomy.

An implanted balloon may also be designed such that it can be resorbed only after certain conditions are met. For instance, a balloon designed to provide containment in a particular region of unhealthy or damaged cortical bone may eventually be resorbed following one or more triggering conditions. In one example, the return of normal physiological conditions would trigger the break down of the balloon implant. The triggering condition may involve relative temperature, pH, alkalinity, redox potential, and osmotic pressure conditions between the balloon and surrounding bone or cancellous materials.

In another example, a controlled chemical or radiological exposure would trigger the break down of the balloon. For instance, a chemically triggered resorption may include, without limitation, a physician prescribed medicament or specially designed chemical delivered to the balloon via oral ingestion or intravenous injection. An electrical charge or current, exposure to high frequency sound, or X-rays may also be used to trigger biological resorption of the balloon.

Resorbable balloons may also provide an implanted balloon with beneficial non structural properties. For instance, soluble compounds contained within a bio-resorbable sheath may have particular clinical benefits. For example, a resorable balloon may break down when healthy cancellous bone remains in contact with the balloon for about six weeks. The breakdown of the balloon may then expose a medicament placed within the balloon structure as an internal coating. Also, the medicament may be incorporated into the balloon matrix itself to provide a time release function for delivering the medicament. The medicament may promote additional bone growth, generally, or in a particular area. Examples of other such complementary benefits include, without limitation, antibacterial effects that prevent infection and agents that promote muscle, nerve, or cartilaginous regeneration.

In use, the balloon 30 is inserted into a bone cavity that has been prepared to allow the balloon to be placed near the damaged cortical bone. Preferably, the cancellous tissue and bone marrow inside the bone and in the area to be treated may be cleared from the region in advance of deploying the balloon. Clearing the treated region may be accomplished by either shifting or relocating the cancellous bone and marrow to untreated regions inside the bone, or alternatively by removing the materials from the bone. Alternatively, cancellous bone and marrow may be cleared with a reamer, or some other device.

Additionally, the bone cavity may be irrigated and/or aspirated. Preferably, the aspiration would be sufficient to remove bone marrow within the region to be restored. In particular, a region as big as the fully deployed balloon should be aspirated in this manner. More preferably, a region exceeding the extent of the fully deployed balloon by about 2 mm to 4 mm would be aspirated in this manner. Clearing the cavity of substantially all bone marrow near or within the treated region may prove especially useful for restoring the bone and incorporating the balloon as a prosthetic device to remain in the cavity.

Clearing substantially all bone marrow from the treated area also may provide better implant synthesis with the cortical bone, and prevent uncontrolled displacement of bone marrow out of areas of damaged cortical bone. For example, a balloon for restoring a vertebral body may further comprise a prosthetic implant which will remain in the restored vertebrae for an extended period of time. Removing substantially all the bone marrow from the region of the vertebrae to be restored might provide better surface contact between the restored bone and the implant.

One skilled in the art would readily appreciate the clinical benefits for preventing the release of marrow or bone filling material to the vascular system or the spinal canal. For example, removing substantially all the bone marrow from the treated region of the bone may reduce the potential for inadvertent and systemic damage caused by embolization of foreign materials released to the vascular system. For vertebral bodies, removing the bone marrow may also reduce the potential for damaging the spinal cord from uncontrolled displacement during deployment of the balloon or a subsequent compression of the vertebrae and implant mass.

Further, the cavity may be treated with a sealant to help prevent or reduce leakage of filler material from the cavity or to help prevent bone materials or body fluids from leaching into the cavity. Generally, sealants comprising fibrin or other suitable natural or synthetic constituents may be used for this purpose. The sealant may be applied at any suitable time or way, such as by spray application, irrigation, flushing, topical application. For example, the sealant may be spray coated inside the cavity prior to or after deployment of the balloon. In addition, the sealant may be applied to the balloon exterior as a coating so that the sealant would be delivered to the cavity as the balloon is deployed.

In another example, the sealant may be placed inside the treated area first, and then an inflatable device may be used to push the sealant outward toward the cavity walls. The inflatable device may be rotated or moved axially in order to apply the sealant. Also, the balloon may not be fully pressurized or may be gradually pressurized while the sealant is being applied.

The viscosity or other properties of the sealant may be varied according to the type of delivery and the procedure used. For example, it is preferred that the sealant is a gel if it is placed inside the cavity and the balloon is used to apply it to the cavity walls. As previously described, each of these optional steps regarding the use of a sealant may be performed after inflation of the balloon, or before, or not at all.

Thereafter, the balloon 30 is inserted into the prepared cavity, where it is inflated by fluid, (e.g., saline or a radiopaque solution) under precise pressure control. Preferably, the balloon 30 is inflated directly against the cortical bone to be restored, by an inflation device 15. In this manner, the deployed balloon presses the damaged cortical bone into a configuration that reduces fractures and restores the anatomy of the damaged cortical bone.

Following fracture reduction, the balloon is deflated by releasing the inflation pressure from the apparatus. Preferably, the balloon may be further collapsed by applying negative pressure to the balloon by using a suction syringe. The suction syringe may be the inflation device itself, or an additional syringe, or any other device suitable for deflating the balloon. After the balloon is sufficiently deflated, the balloon may be removed from the cavity, and the bone cavity may be irrigated or aspirated. Optionally, the cavity also may be treated with a sealant. The cavity then can be filled with bone filler material. The bone filler material may be natural or synthetic bone filling material or any other suitable bone cement. As previously described, each of these optional steps may be performed after inflation of the balloon, or before, or not at all.

As described more fully below, the timing of the deflation of the balloon and the filling of the cavity with bone filler material may be varied. In addition, the balloon may not be deflated prior to completing the surgical procedure. Instead, it may remain inside the bone cavity for an extended period. Thus, the method of the present invention relates to creating a cavity in cancellous bone, reducing fractures in damaged cortical bone with a medical balloon, restoring the natural anatomy of the damaged bone, and filling the restored structure of the bone with filling material.

The inflatable device may also be adapted to serve as a prosthetic device outside of a bone. One example is that the balloon may be used as an artificial disk located between two adjacent vertebrae. The use of an inflatable device in this manner may allow for replacement of the nucleus of the treated disk, or alternatively may be used for full replacement of the treated disk. Portions of the treated disk may be removed prior to deploying the inflatable device. The amount of disk material removed may depend upon the condition of the treated disk and the degree to which the treated disk will be replaced or supported by the inflatable device. The treated disk may be entirely removed, for instance, when the inflatable device serves as a complete disk replacement. If the inflatable device will serve to support or replace the nucleus or other portion of the treated disk, then less material, if any, may need to be removed prior to deployment.

The construction and shape of the inflatable device may vary according to its intended use as either a full disk replacement or a nuclear replacement. For instance, an inflatable device intended to fully replace a treated disk may have a thicker balloon membrane or have coatings or other treatments that closely replicate the anatomic structure of a natural disk. Some features include coatings or textures on the outer surface of the inflatable device that help anchor it or bond it to the vertebral endplates that interface with the artificial disk. The balloon membrane also may be configured to replicate the toughness, mechanical behavior, and anatomy of the annulus of a natural disk. The filler material likewise may be tailored to resemble the mechanical behavior of a natural disk.

In another example, if the inflatable device is intended to treat only the nucleus of the disk, the balloon may be designed with a thin wall membrane that conforms to the interior of the natural disk structures that remain intact. In addition, the balloon membrane may be resorbable so that the filler material remains after the inflatable device has been deployed. Alternatively, the balloon membrane may be designed and configured to allow the balloon to be lysed and removed from the patient during surgery. One advantage of this design would be that the balloon may function as a delivery device that allows interoperative measurement of the volume of the filler material introduced into the patient. In addition, this design allows for interoperative adjustment of the volume, so that filler material can be added or removed according to the patient's anatomy before permanent deployment. Other design features of the inflatable device and filler material described herein for other embodiments or uses also may be utilized when designing a balloon as an artificial disk.

In one embodiment of an artificial disk, the balloon is inflated with a radio-opaque material to restore the natural spacing and alignment of the vertebrae. The inflating solution or material may be cured or reacted to form a viscous liquid or deformable and elastic solid. Preferably, such a balloon may comprise an implant possessing material and mechanical properties which approximate a natural and healthy disk. For instance, the balloon may be designed for long term resistance to puncture and rupture damage, and the filler material may be designed and configured to provide pliable, elastic, or fluid like properties. Generally, filler material for a replacement disk balloon may comprise any suitable substance, including synthetic and bio-degradable polymers, hydrogels, and elastomers. For example, a balloon may be partially filled with a hydrogel that is capable of absorbing large volumes of liquid and undergoing reversible swelling. A hydrogel filled balloon may also have a porous or selectively porous containment membrane which allows fluid to move in and out of the balloon as it compressed or expanded. The filler material may also be designed and configured to form a composite structure comprising a solid mass of materials.

Balloons of the present invention also may be adapted for use as a distraction instrument and an implant for interbody fusion, such as for the lumbar or cervical regions. For instance, a inflatable device of the present invention may be used for posterior lumbar interbody fusion (PLIF). A laminotomy, for example, may be performed to expose a window to the operation site comprising a disc space. The disc and the superficial layers of adjacent cartilaginous endplates may then be removed to expose bleeding bone in preparation for receiving a pair of PLIF spacers. A balloon of the present invention may then be inserted into the disk space and inflated to distract the vertebrae. The controlled inflation of the balloon may ensure optimum distraction of the vertebrae and facilitate maximum implant height and neural for aminal decompression. Fluoroscopy and a radio-opaque balloon inflation fluid may assist in determining when a segment is fully distracted.

If the balloon is to serve as a distraction instrument, a bone or synthetic allograft along with cancellous bone graft or filler material may then be implanted into contralateral disc space. Once the implant and other materials are in the desired position, the balloon may be deflated and removed from the disk space and a second implant of the same height may be inserted into that space.

If the balloon is to serve as a spacer for intervertebral body fusion, the balloon may be inflated with a filler material that sets to form an synthetic allograft implant in vivo. Once the implant has been adequately formed, the balloon may be lysed and removed from the disk space. In another example, the inflated balloon is left intact and is separated from the catheter to remain within the disk space as a scaffold for new bone growth. As previously described, a balloon implant also may be resorbed by physiological conditions and expelled from the patient or transformed and remodeled into new bone growth.

For techniques involving multiple deployments of balloons or filler material, different radiographic signatures may be used for each deployment to enhance the quality of fluroscopic imagery and to assist the surgeon in interpreting spacial relationships within the operation site. The use of different radiographic signatures may be used, for example, with inflatable devices when they are used as instruments (such as a bone restoration tool or as a distraction device), when they are used to deliver bone filler material, or when they are used as implants. Additionally, the use of different radiographic signatures may be utilized for multiple deployment of filler material. For instance, a technique involving the deployment of two balloons between adjacent vertebrae might benefit from such an approach. Similarly, other orthopedic procedures, such as vertebroplasty, also may involve the deployment of multiple balloons having different radiographic signatures. In another example, when the balloon of the present invention is used as a PLIF spacer, the filler material within the first of two intervertebral spacer implant balloons may be provided with less radio-opacity then the second implant. As one skilled in the art would readily appreciate, varying the radio-opacity of the respective implants would facilitate fluoroscopic monitoring and deployment of the second implant. In particular, this would prevent a deployed implant on a first side from blocking the fluoroscopic image of a second implant. This advantage may also be realized when differing radiographic signatures are used in any situation involving multiple deployments, such as for multiple deployments of balloons or filler materials as described above.

The radio-opacity of each implant may be varied by incorporating different concentrations of a radio-opaque material within the filler material which inflates the balloon. For example, filler materials comprising two different concentrations of barium sulfate may be used. Similarly, different radio-opaque materials having distinguishable flouroscopic characteristics may be used.

Figure 2:
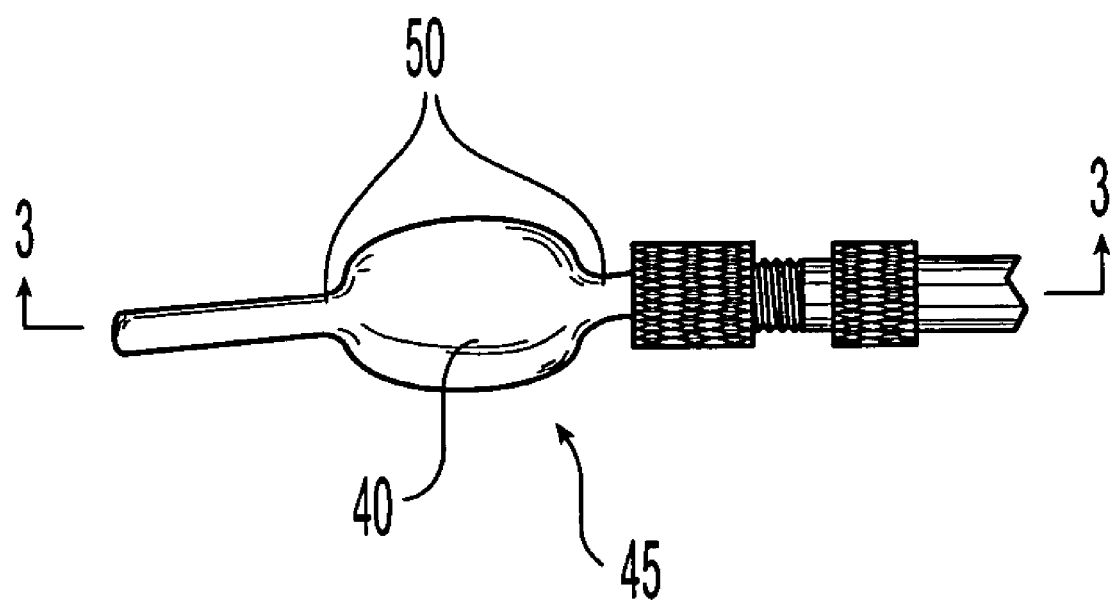
FIG. 2 shows a perspective view of the balloon of FIG. 1

FIG. 2, shows a medical balloon 40 of the construction described above inflated to approximately 200 psi. Preferably, the balloon 40 is made from a single layer of polyurethane material. Multiple balloon layers, and coatings of other materials such as silicone may also be used. For example, the silky texture of an outer silicone layer or coating may be used to facilitate insertion of the balloon 40 or to achieve another clinical objective. One skilled in the related art would recognize that additional materials, layers, and coatings, and combinations thereof, may be used to improve the serviceability of the balloon 40, for example, by increasing the ability of the inflated vessel to resist puncture and tearing. Preferably, the single wall thickness of the balloon 40 may range from approximately about 1.5 mils to about 2.5 mils. A single wall thickness, however, ranging from about 0.5 mil to about 3.5 mils also may be preferred for particular applications. The thickness of optional layers or coatings preferably may range from approximately about 0 mils to about 4 mils. Additionally, radio-opaque indicia (not shown) may be applied to the exterior surface of the balloon 40 to provide an enhanced visual means for assessing the degree of inflation and collapse.

A composite balloon comprising at least two materials that may serve as a reinforcing component and as a boundary forming component. The boundary forming component may be any suitable material used for forming a balloon. Examples of such materials are described more fully herein. The reinforcing component may provide added tensile strength to the balloon by picking up tensile stress normally applied to the boundary forming component of the balloon. The reinforcing component may be designed and configured to distribute these forces evenly about its structure, or may be designed and configured to form a space frame for the deployed balloon structure. The reinforcing component may facilitate better shape control for the balloon and provide for a thinner boundary forming component.

In one embodiment the reinforcing member component may be a braided matrix extending over selected areas of the balloon. In another embodiment, the braided matrix may enclose the balloon structure in its entirety. In another embodiment, braided matrix is on the inside of the boundary forming component of the balloon. Conversely, in another embodiment the braided matrix is located on the outside of the boundary forming component of the balloon. In one embodiment, the braided matrix is located within the boundary forming component. For example, a boundary forming component comprising a membrane might include a braided matrix within the membrane. The reinforcing strength of the braided matrix may be influenced by the type of material from which it is constructed, or by the shape and dimension of the individually braided reinforcing members.

Additionally, the reinforcing strength of the braided matrix may be determined by the tightness of the weave. For example, a more dense pattern for the braided matrix might provide greater strength but less flexability, than a less dense weave of a similar pattern. Also, different patterns may have different combinations of physical characteristics. The angle of the intersecting braided members may also be varied to optimize the physical properties of the balloon. The braided matrix may therefore be customized to provide a certain combination of physical or chemical properties. These properties may include tensile and compressive strength, puncture resistance, chemical inertness, shape control, elasticity, flexability, collapsability, and ability to maintain high levels of performance over the long term. The braided materials may be comprised of any suitable material including nitinol, polyethylene, polyurethane, nylon, natural fibers (e.g., cotton), or synthetic fibers. One firm which manufactures braided matrices of the type described above is Zynergy Core Technology.

As noted above the boundary forming component may comprise a synthetic membrane formed from polyurethane or other materials as described for the general balloon construction. The membrane may be coated on the exterior to enhance non-reactive properties between the balloon and the body, or to ensure that a balloon will not become bonded to the balloon inflation materials. Thus, a lysed balloon may be withdrawn without significant disturbance to the filled cavity. It is expected that a balloon formed from a membrane and braided matrix may designed to operate at an internal pressure of about 300 psi.

Figure 3:
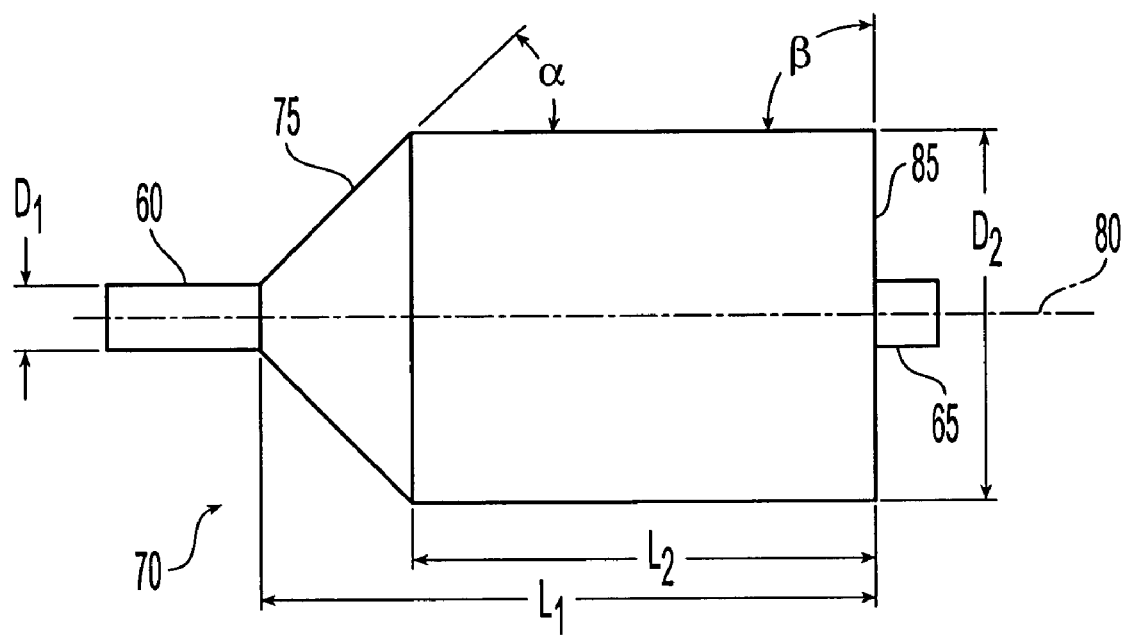
FIG. 3 shows a sectional view along line 3-3 of FIG. 2.

As previously described, the size and configuration of the inflation device may vary according to the particular bone to be restored. FIG. 3 illustrates a general construction of a balloon of the present invention. The features described in FIG. 3. include: D1 (the outer diameter of the balloon tubing); D2 (the outer diameter of the working body of the balloon);

L1 (the length of the balloon); L2 (the working length of the balloon 70); α (the tapered angle of the balloon's proximal end); and β (the angle of the balloon's distal end). Angles α and β are measured from the longitudinal axis 80 of the balloon. Table 1 presents preferred values for the features of the balloon construction depicted in FIG. 3, as they may apply to particular bone anatomies. Values presented in range 1 represent generally preferred dimensions and characteristics. Values presented in range 2, by comparison, represent more preferred criteria.

TABLE 1

PREFERRED AXIAL BALLOON EMBODIMENTS

| Target Bone Anatomy | Preferred Size | D1 (mm) | D2 (mm) | L1 (mm) | L2 (mm) | α (deg.) | β (deg.) |
|---|---|---|---|---|---|---|---|
| Vertebral Body | Range 1 | 1.0-3.5 | 5-30 | 10-35 | 5-25 | 25-80 | 50-105 |
| | Range 2 | 1.5-3.0 | 8-26 | 15-25 | 12-20 | 45-65 | 60-86 |
| Distal Radius | Range 1 | 1.0-3.5 | 5-25 | 10-45 | 6-40 | 25-80 | 50-105 |
| | Range 2 | 1.5-3.0 | 8-14 | 15-25 | 12-22 | 45-65 | 60-86 |
| Calcaneus | Range 1 | 1.0-3.5 | 5-25 | 5-35 | 3-33 | 25-80 | 50-105 |
| | Range 2 | 1.5-3.0 | 8-12 | 8-12 | 6-13 | 30-50 | 55-80 |
| Tibial Plateau | Range 1 | 1.0-3.5 | 5-40 | 15-60 | 11-56 | 25-80 | 50-105 |
| | Range 2 | 1.5-3.0 | 12-30 | 20-40 | 16-36 | 45-65 | 60-86 |

As described in Table 1, a preferred balloon for a vertebral body would have tubing 60 with outer diameter D1 that ranges from about 1.5 mm to about 3.0 mm. The tubing 60 preferably would also be suitable for attachment to a 16 gauge catheter. As best shown in FIG. 3, the balloon tip 65 may be sized according to the catheter requirements. Additionally, outer diameter D2 would preferably range from about 8 mm to about 26 mm, and more preferably would be between about 12 mm and about 20 mm. Similarly, the proximal end 75 of the balloon 70 may taper at an approximately uniform angle α from the longitudinal axis 80 of the balloon 70. Preferably, angle α ranges from about 25 degrees to about 80 degrees, and more preferably ranges from about 45 to 60 degrees. The distal end 85 of the balloon 70 may also taper at an approximately uniform angle β from the longitudinal axis 80 of the balloon 70. Preferably, the angle β ranges from about 90 degrees to about 50 degrees, and more preferably ranges from about 60 to 86. Further, length L1 of the balloon 70, preferably ranges from about 15 mm to about 30 mm, and the working length L2 of the balloon 70 preferably ranges from about 10 mm to about 20 mm. More preferably, however, length L1 of the balloon 70 ranges from about 20 mm to 25 mm, and the working length L2 of the balloon 70 ranges from about 12 mm to about 15 mm.

The preferred embodiments described above include preferred sizes and shapes for balloons comprising a braided matrix and membrane. As previously noted such a balloon may be adapted to remain with a vertebral body, as a prosthetic device or implant.

Figure 4:
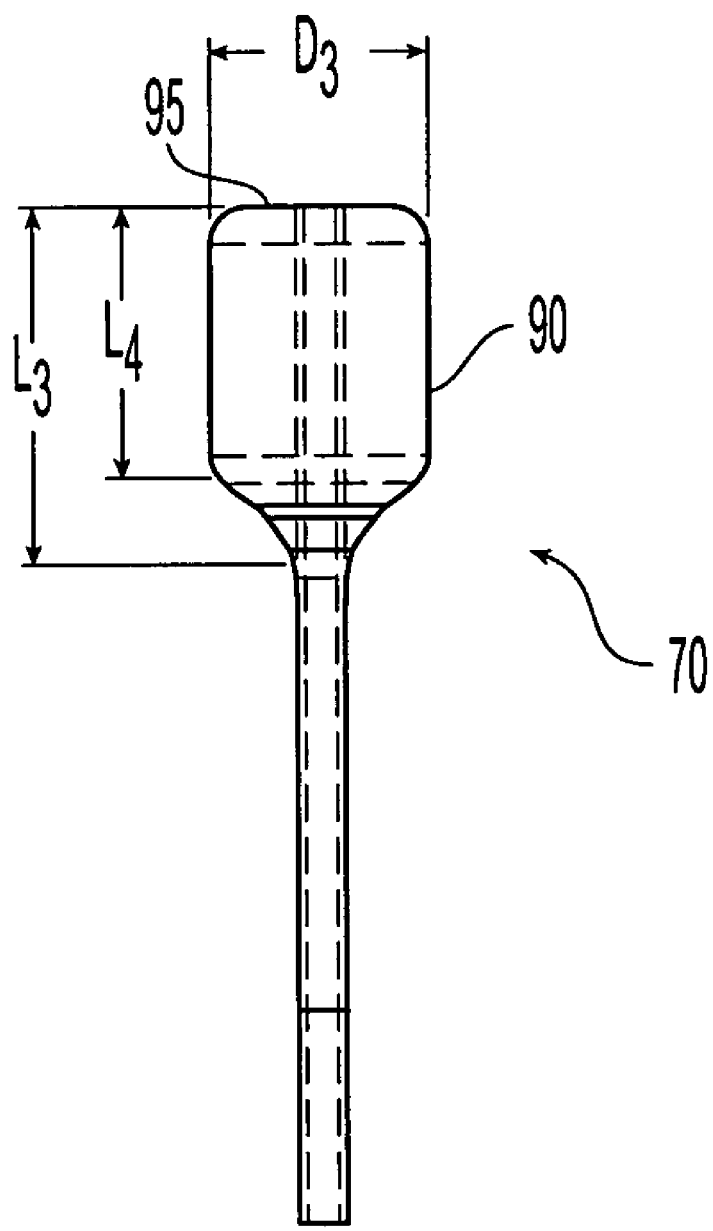
FIG. 4 shows a partial sectional view along the longitudinal axis of another embodiment of the balloon catheter of FIG. 1.
Figure 5:
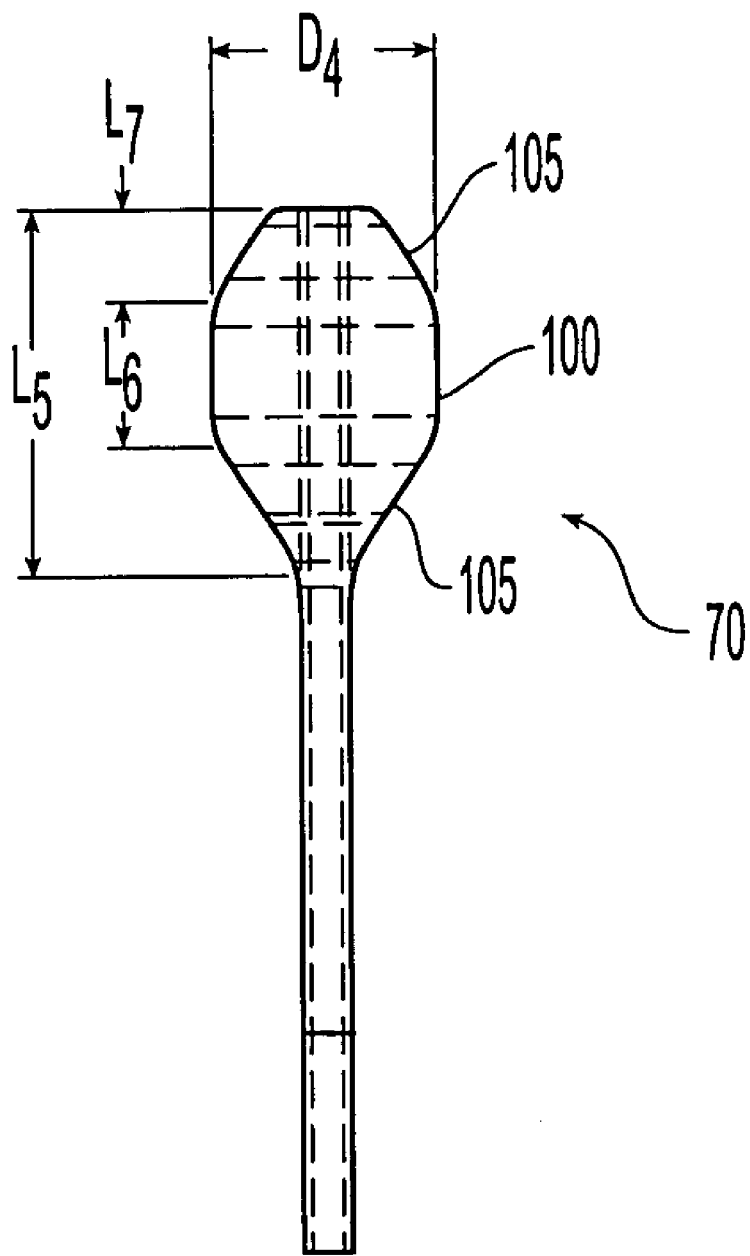
FIG. 5 shows a partial sectional view along the longitudinal axis of another embodiment of the balloon catheter of FIG. 1.
Figure 6:
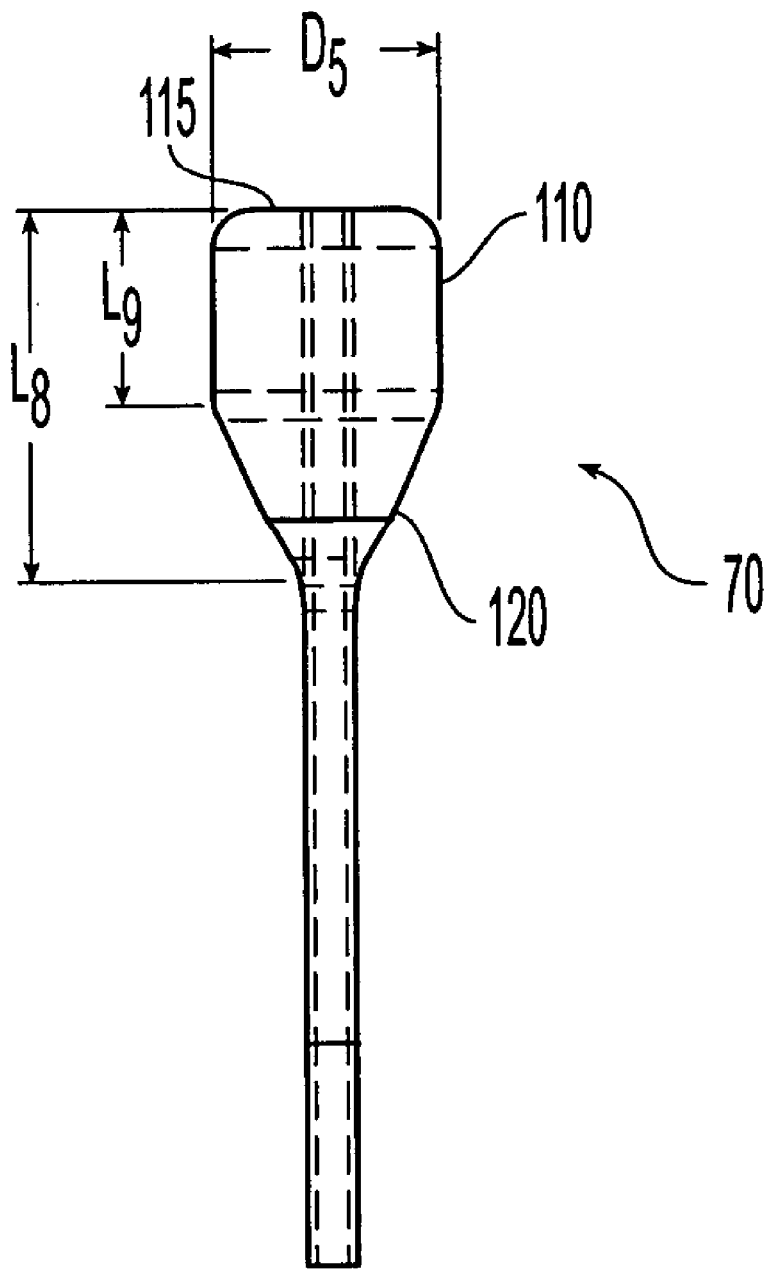
FIG. 6 shows a partial sectional view along the longitudinal axis of another embodiment of the balloon catheter of FIG. 1.

FIGS. 4-6 show preferred embodiments of the axial balloon 70 described in FIG. 3 and Table 1. Although, the following discussion is directed toward exemplary balloon embodiments for deployment in vertebral bodies, these balloons may be used in any suitable bone. Thus, the dimensions and configurations of the balloon styles described in this figures may be varied to accommodate the type of bone or cavity in which the balloon is to be deployed.

FIG. 4 depicts a balloon embodiment style with an uniform bulge 90 having an axially uniform diameter D3 with a blunt distal end 95. In one embodiment, the total length L3 is about 20 mm, the working length L4 is about 15 mm, and the outer diameter D3 is about 12 mm. In another embodiment, the total length L3 is about 20 mm, the working length L4 is about 15 mm, and the outer diameter D3 is about 8 mm. In yet another embodiment, the total length L3 is about 15 mm, the working length L4 is about 10 mm, and the outer diameter D3 is about 8 mm.

FIG. 5 depicts a balloon embodiment style with a central bulge 100 having a constant outer diameter D4 in a central portion of the balloon 70, while having uniformly tapered ends 105. In one embodiment, a balloon with a central bulge has a total length L5 of about 20 mm, a working length L6 of about 8 mm, a horizontal length L7 of the tapered distal end of about 5 mm, and an overall outer diameter D4 of about 12 mm. In another embodiment, the total length L5 is about 20 mm, the working length L4 is about 8 mm, the horizontal length L7 of the tapered distal end is about 5 mm, and the overall outer diameter D4 of the balloon is about 8 mm. In another embodiment, the total length L5 is about 15 mm, the working length L4 is about 8 mm, the horizontal length L7 of the tapered distal end is about 5 mm, and the overall outer diameter D4 of the balloon is about 8 mm. One skilled in the art would appreciate that the tapered end of this balloon style may have other configurations. For instance, the balloon may have a series of uniform tapered lengths, rather than a single uniform tapered end. Also, the balloon may have a curved tapered end, rather than one or more uniform tapered lengths.

Similarly, the balloon may have a combination of uniform and curved lengths comprising the tapered end of the balloon. The tapered end also may be unsymmetrical about the central axis of the balloon. A balloon comprising a braided matrix and membrane components may be of particular use in developing balloons having a tapered end or unsymmetrical geometry because the braided material can be used to improve shape control or create a space frame for the deployed balloon.

FIG. 6 depicts a balloon embodiment style with an distal bulge 110 having a constant outer diameter D5 in a region abutting a blunt distal end 115, and a uniformly tapered proximal end 120. In one embodiment, the total length L8 is about 20 mm, the working length L9 is about 8 mm, and the outer diameter D5 is about 12 mm. In another embodiment, the total length L8 is about 20 mm, the working length L9 is about 8 mm, and the outer diameter D5 is about 8 mm. In yet another embodiment, the total length L8 is about 15 mm, the working length L9 is about 8 mm, and the outer diameter D5 is about 8 mm. As previously described, one skilled in the art would appreciate that the tapered end of this balloon style may have other configurations. Further, the surprising advantages of the balloon styles depicted in FIGS. 4-6 may be achieved by using a curved or bent catheter.

Figure 7:
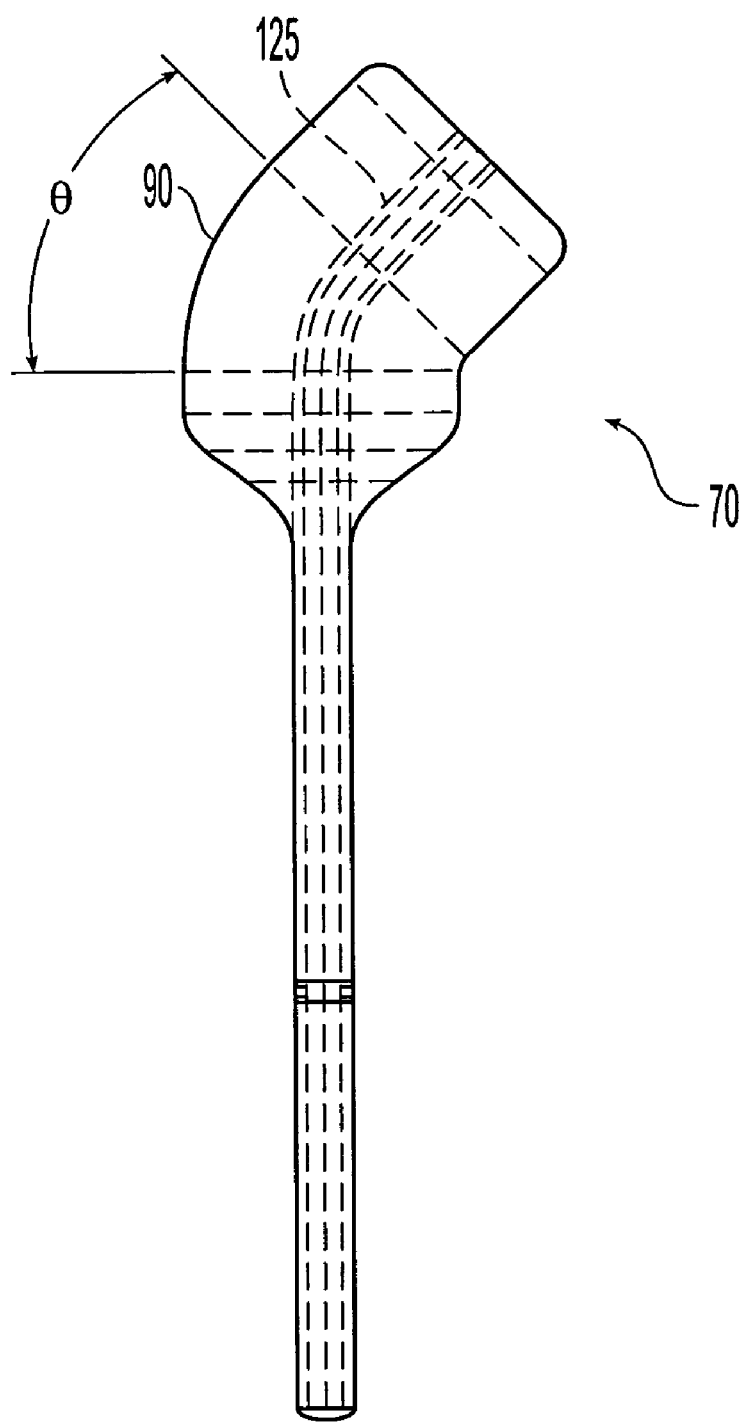
FIG. 7 shows a partial sectional view along the longitudinal axis of another embodiment of the balloon catheter of FIG. 1.

FIG. 7 depicts an exemplary embodiment of the balloon of FIG. 4 having a bend of angle θ along its working length. One skilled in the art would appreciate that more than one bend in the catheter may be used to provide further surprising advantages to the device. Similarly, the catheter may be constructed from a shape memory metal so that the balloon may positioned or deployed in one configuration and then repositioned or deployed in a second configuration at the selective control of the surgeon. Thus, a balloon may be configured for optimal positioning, deployment, and removal from the target cavity. For instance, balloons fitted to shape memory catheters may be deployed to restore the natural anatomy of right and left bones, or the left and right sides of bones with a sagittal plane of symmetry. Preferably, as shown in FIG. 7 the bend of angle θ is obtuse. In another embodiment, the balloon catheter may be incorporate a number of successive bends to create a balloon with parallel central axes.

Similarly, the balloon styles depicted in FIGS. 4-6 and the more general balloon configurations defined by FIG. 3 and Table 1 may be angled from the central catheter.

Figure 8:
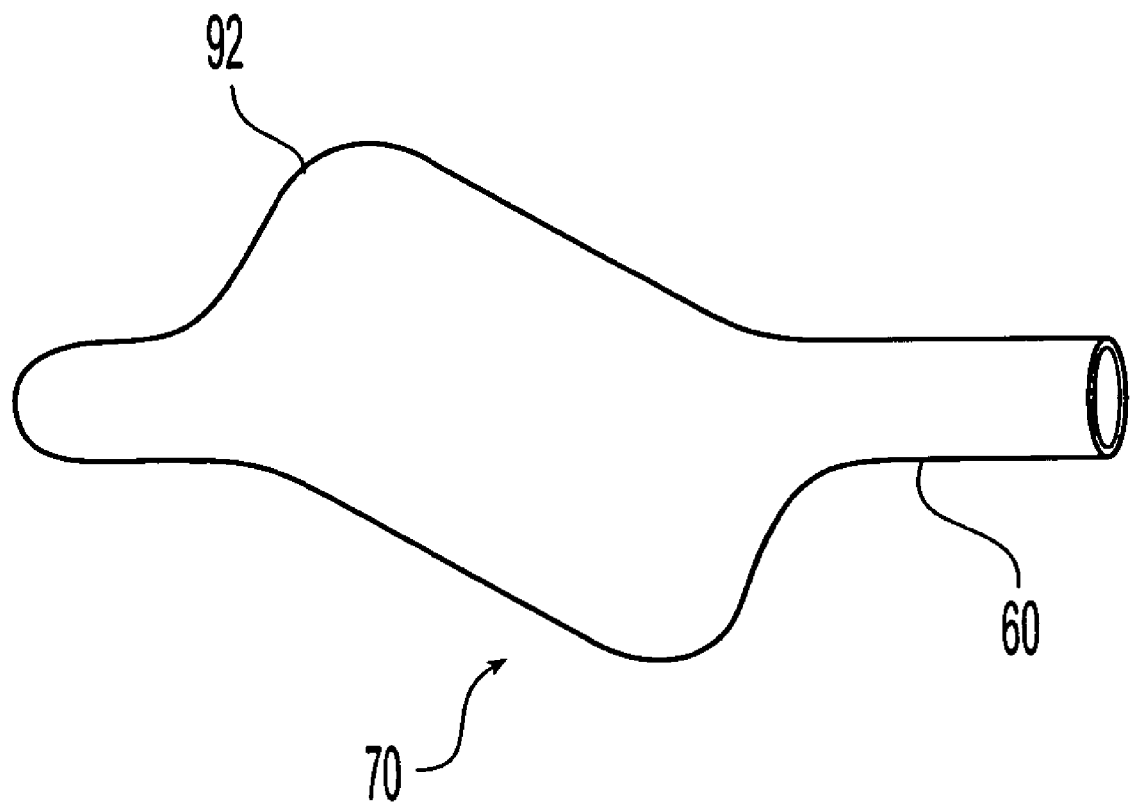
FIG. 8 shows a partial sectional view along the longitudinal axis of another embodiment of the balloon catheter of FIG. 1.

FIG. 8, depicts an exemplary embodiment of balloon 70 with an angled uniform bulge 92. Angle δ, preferably, is acute. One skilled in the art would appreciate that balloons shaped for particular bone cavities or with additional surprising advantages may be developed by using an angled or curved catheter made from shape memory metal as previously described.

Referring to FIGS. 9-16, preferred balloon configurations may also be developed from offset balloons, including constructions with curved or angled catheters. FIGS. 9-12 depict general embodiments of an exemplary offset balloon.

Figure 9:
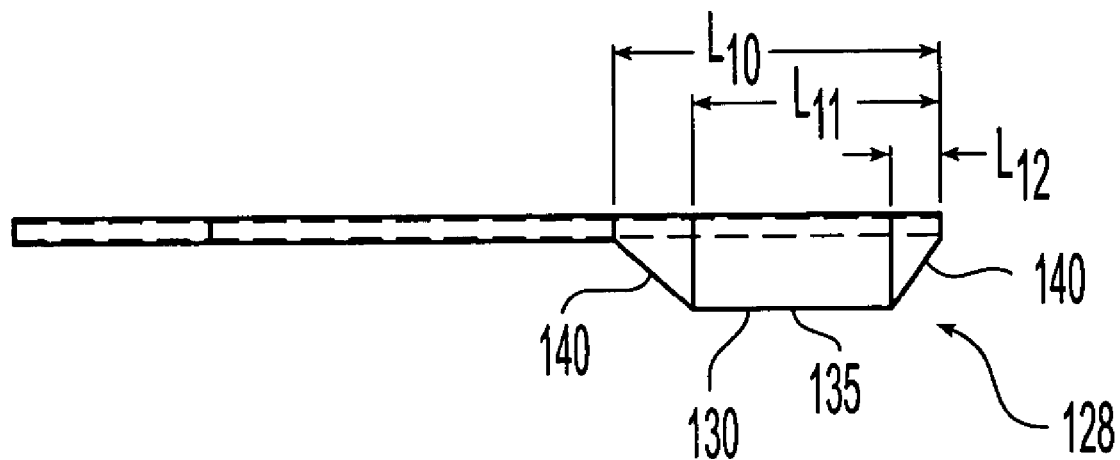
FIG. 9 shows a partial sectional view along the longitudinal axis of another embodiment of the balloon catheter of FIG. 1.
Figure 10:
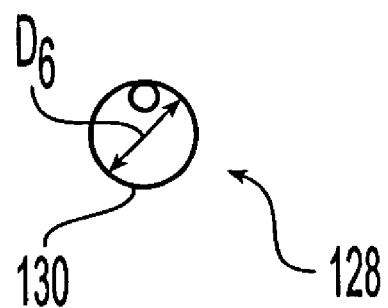
FIG. 10 shows a sectional view perpendicular to the longitudinal axis of the balloon of FIG. 9.

FIGS. 9 and 10 show an embodiment style of a balloon 128, which is characterized by an offset balloon 130 having an uniform circular bulge 135 in the center of the balloon 130 and uniformly tapering ends 140. The total length L10 of the balloon 130 is divided into a proximal tapered end, a central working section having uniform outer diameter D6, and a distal tapered end. The horizontal length of each of these sections may be defined with respect to the distal end of the balloon. For example, length L11 represents the horizontal distance of the distal tapered end plus the length of the central working section. Length L12 represents the horizontal length of the distal tapered end. Table 2 presents general preferred and preferred size ranges for this balloon configuration by target bone anatomy. Values presented in range 1 represent generally preferred dimensions and characteristics. Values presented in range 2, by comparison, represent more preferred criteria.

TABLE 2

PREFERRED EMBODIMENTS FOR
OFFSET BALLOONS WITH CIRCULAR CROSS-SECTION

| Target geometry | Preferred Size | D6 (mm) | L10 (mm) | L11(a) (mm) | L12 (mm) |
|---|---|---|---|---|---|
| Vertebral Body | Range 1 | 5-30 | 10-35 | 8-25 | 0-5 |
|  | Range 2 | 6-20 | 15-25 | 12-22 | 1-3 |
| Distal Radius | Range 1 | 5-25 | 10-45 | 6-40 | 0-5 |
|  | Range 2 | 8-14 | 15-25 | 12-22 | 1-3 |
| Calcaneus | Range 1 | 5-25 | 5-35 | 3-33 | 0-5 |
|  | Range 2 | 8-12 | 12-28 | 8-24 | 1-3 |
| Tibial Plateau | Range 1 | 5-40 | 15-60 | 11-56 | 0-5 |
|  | Range 2 | 12-30 | 20-40 | 16-36 | 1-3 |

(a) Where L11 includes L12

As described in Table 2, the following exemplary embodiments are primarily directed toward vertebral bodies. In one embodiment, the total length L10 is about 20 mm, the working length L11 is about 15 mm, the horizontal distance L12 of the tapered distal end is about 3 mm, and the outer diameter D6 of the circular bulge is about 6 mm. In another embodiment, the balloon has similar dimensions except that the outer diameter D6 is about 8 mm. In yet another embodiment, the balloon diameter D6 is about 12 mm.

Figure 11:
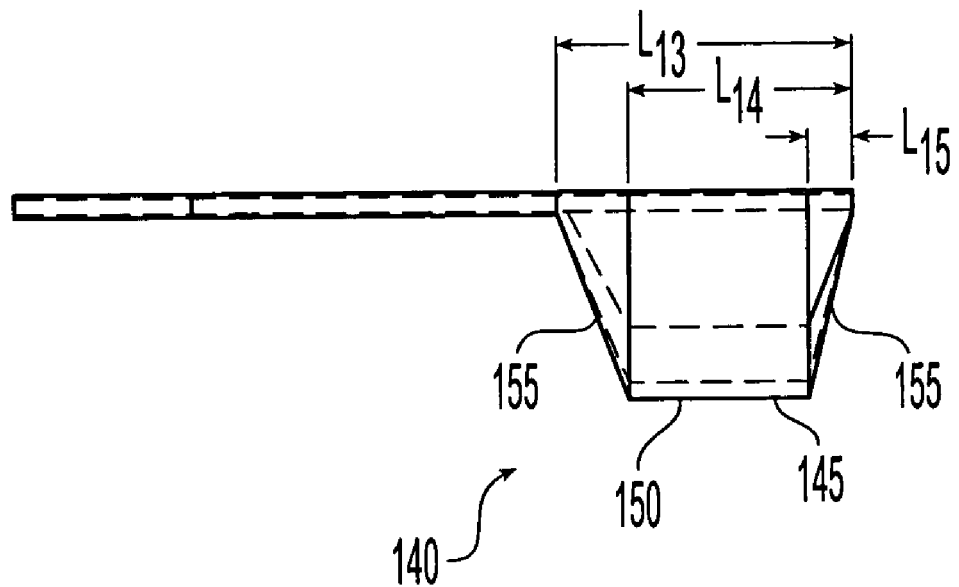
FIG. 11 shows a partial sectional view along the longitudinal axis of another embodiment of the balloon catheter of FIG. 1.
Figure 12:
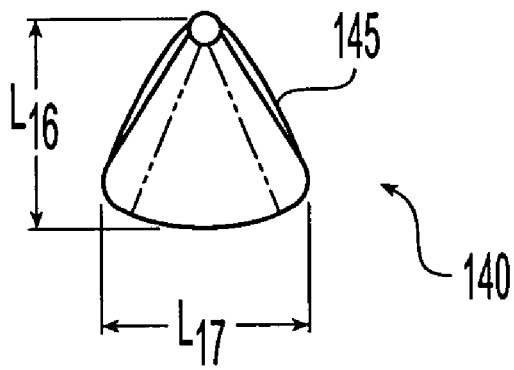
FIG. 12 shows a sectional view perpendicular to the longitudinal axis of the balloon of FIG. 11.

FIGS. 11 and 12, by contrast, show an embodiment style of a balloon 140, which is characterized by an offset balloon 145 having a non-uniform circular bulge 150 in the center of the balloon 145 and uniformly tapering ends 155. The total length L13 of the balloon 140 is divided into a tapered distal end, central working section, and proximal tapered end. The balloon has non uniform cross-section which may be defined by vertical length L16 and cross sectional width L17. Length L14 represents the horizontal distance from the distal end of the balloon. Table 3 presents general and preferred size ranges for this balloon configuration by target bone anatomy. Values presented in range 1 represent generally preferred dimensions and characteristics. Values presented in range 2, by comparison, represent more preferred criteria.

TABLE 3

PREFERRED EMBODIMENTS FOR
OFFSET BALLOONS WITH NON CIRCULAR CROSS-SECTION

| Target geometry | Preferred Size | L13 (mm) | L14 (mm) | L15 (mm) | L16 (mm) | L17 (mm) |
|---|---|---|---|---|---|---|
| Vertebral Body | Range 1 | 10-35 | 8-25 | 0-5 | 5-30 | 5-30 |
|  | Range 2 | 15-25 | 12-22 | 1-3 | 6-20 | 6-20 |
| Distal Radius | Range 1 | 10-45 | 6-40 | 0-5 | 5-25 | 5-25 |
|  | Range 2 | 15-25 | 12-22 | 1-3 | 8-14 | 8-14 |
| Calcaneus | Range 1 | 5-35 | 3-33 | 0-5 | 5-25 | 5-25 |
|  | Range 2 | 12-28 | 8-24 | 1-3 | 8-12 | 8-12 |
| Tibial Plateau | Range 1 | 15-60 | 11-50 | 0-5 | 5-40 | 5-40 |
|  | Range 2 | 20-40 | 16-36 | 1-3 | 12-30 | 12-30 |

As described in Table 3, the following exemplary embodiment is primarily directed toward vertebral bodies. In one embodiment, the total length L13 is about 20 mm, the working length L14 is about 15 mm, and the horizontal distance L15 of the tapered distal end is about 3 mm. Further, the vertical height L16 and the lateral width L17 of the balloon 145 are 14 mm and 14 mm, respectively.

Figure 13:
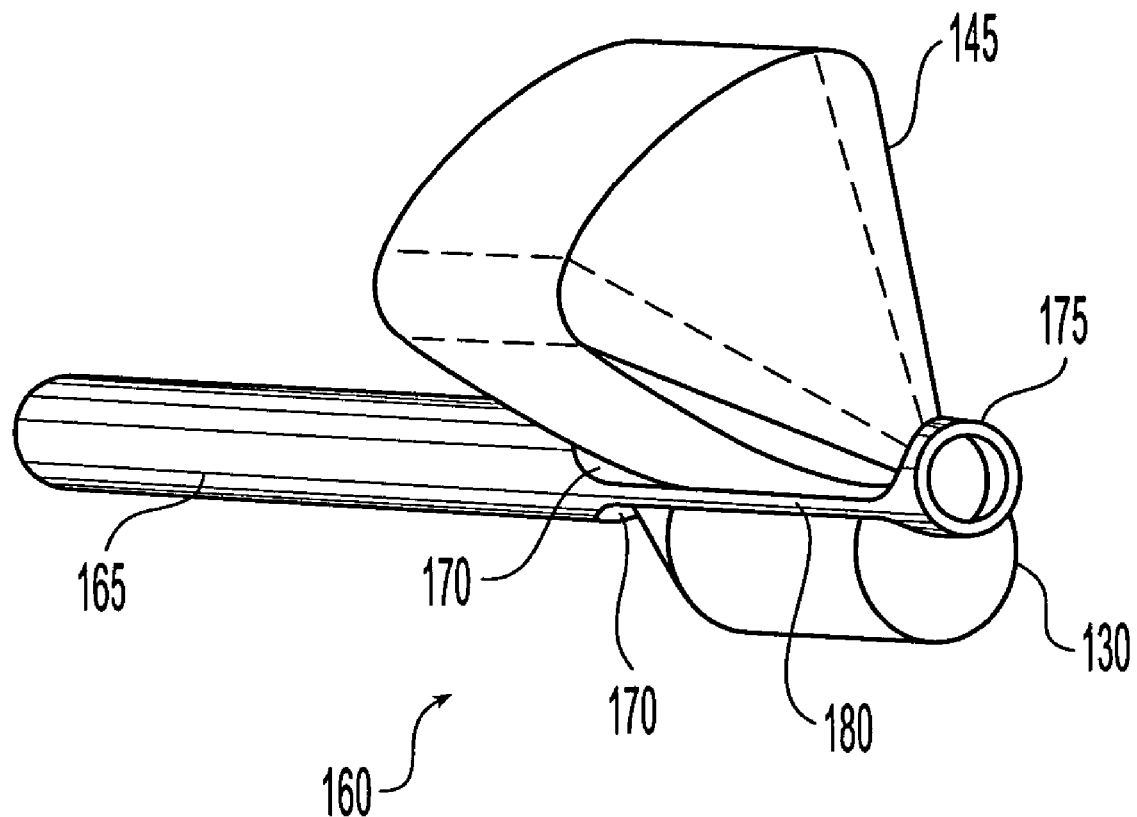
FIG. 13 shows a perspective view of another embodiment of the balloon of FIG. 1.
Figure 14:
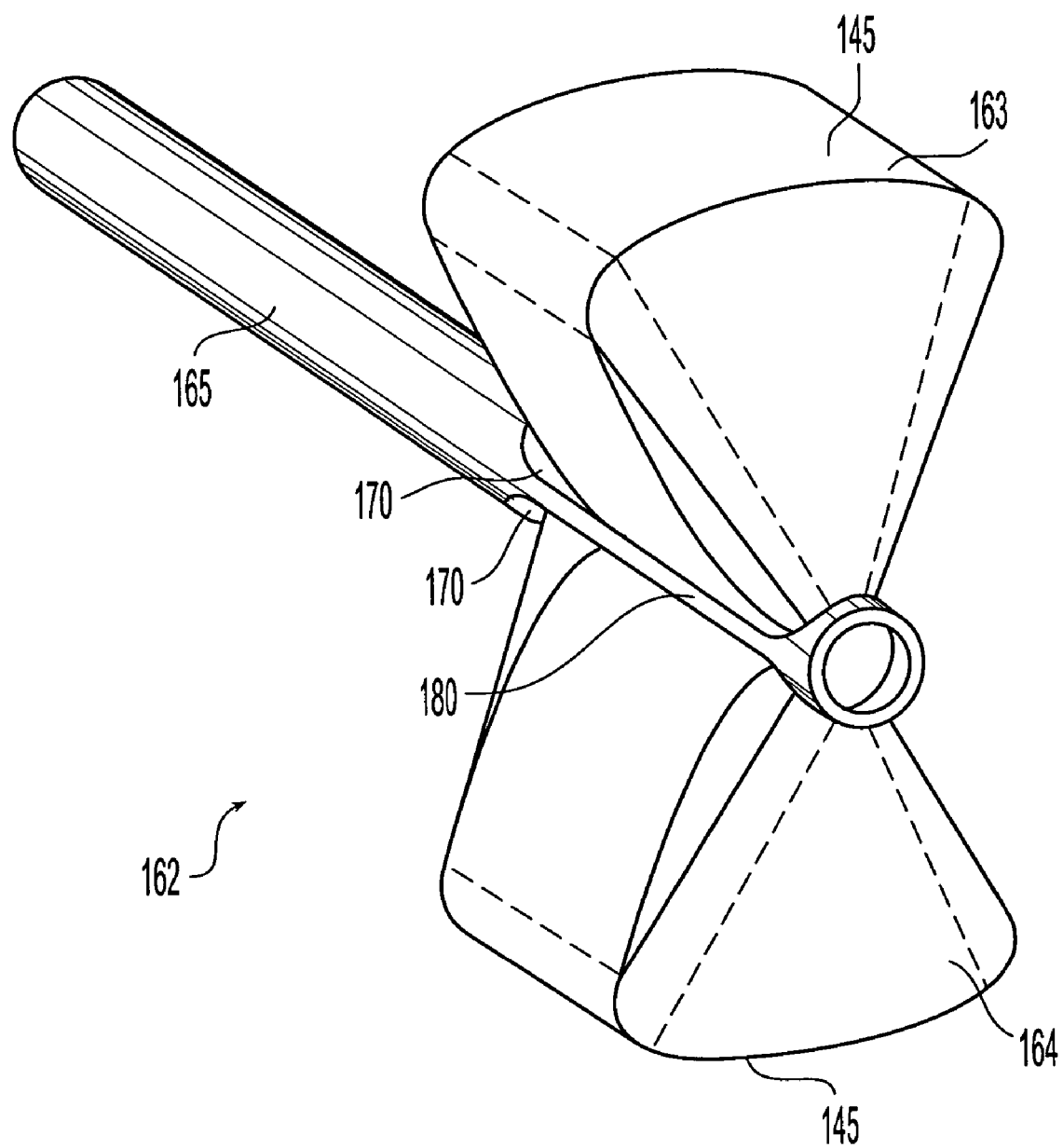
FIG. 14 shows a perspective view of another embodiment of the balloon of FIG. 1.
Figure 15:
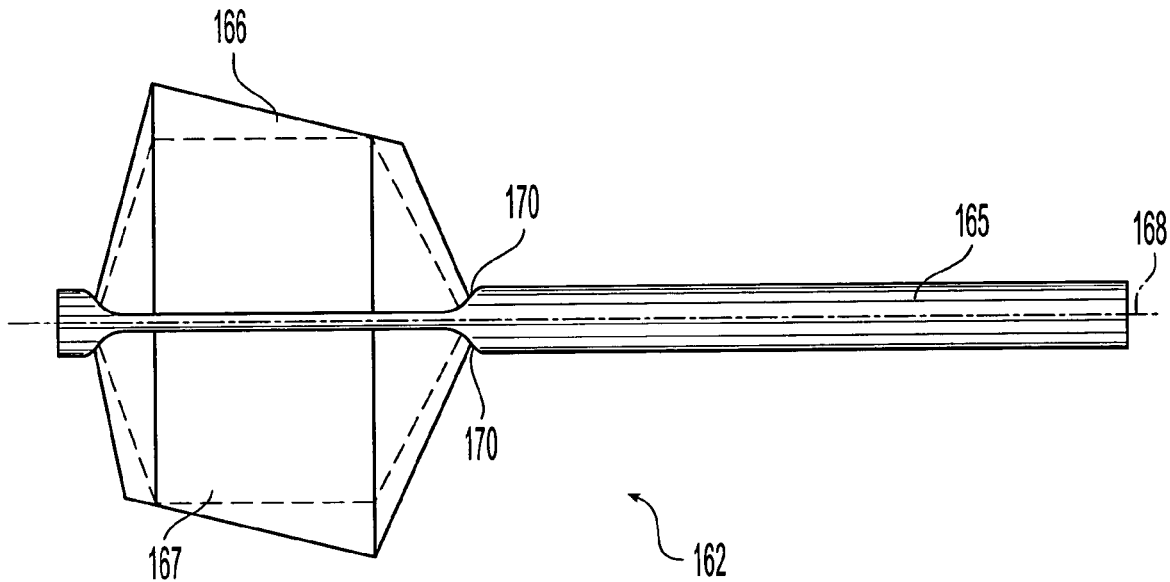
FIG. 15 shows an elevation view of another embodiment of the balloon of FIG. 1.

Referring to FIGS. 9 and 12, these general balloon embodiments and the preferred dimensions presented in Tables 2 and 3 may be combined to create complex balloons, which are inflatable structures comprised of a plurality of balloons. For instance, FIG. 13 depicts an embodiment of a complex balloon 160, and a catheter 165 adapted to deploy two inflatable structures 130 and 145. In this exemplary embodiment, the balloons 130 and 145 which comprise the complex inflatable structure 165 are fully seated within the catheter 160, and are deployed through openings 170 around the catheter 165 circumference. FIG. 14 depicts an embodiment of a single balloon 162 with two chambers 163 and 164 each of which are shaped like offset balloon style 145. By contrast, FIG. 15 depicts another embodiment of the balloon of FIG. 14, wherein the balloon chambers 166 and 167 are angled with respect to the longitudinal axis 168 of the balloon catheter 165. Additionally, in other general embodiments of complex balloons as depicted in FIG. 14, balloons with circular cross-sections, or other suitable geometric shapes may be used.

Figure 16:
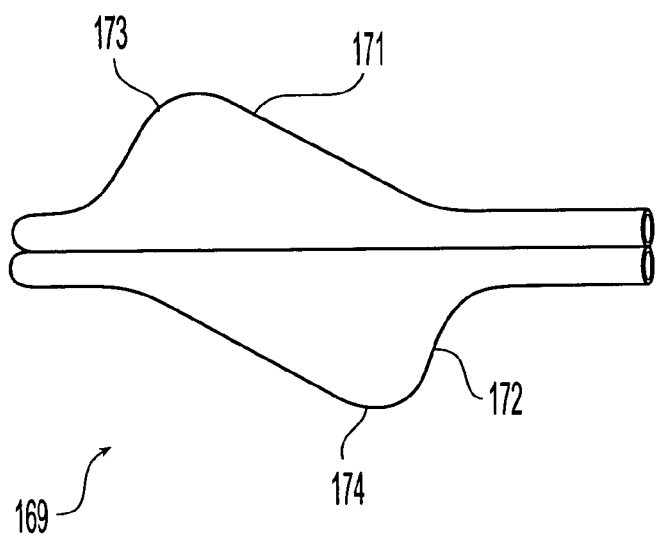
FIG. 16 shows an elevation view of another embodiment of the balloon of FIG. 1.

In yet another exemplary embodiment of a complex balloon, FIG. 16 shows balloon 169 comprising two individual balloons 171 and 172, each having a tapered bulge 173 and 174 that produce a complex and angled embodiment of the balloon of FIG. 14. As the foregoing discussion suggests, complex balloons may be constructed for particular bone geometries or clinical purposes. One skilled in the art would appreciate that angled balloons such as those depicted in FIGS. 15 and 16 can be made for an anatomically correct fit, as previously described, without requiring an angled catheter shaft. One skilled in the art would further appreciate the potential reduction in cost an angled balloon construction might posses over a similarly shaped angled catheter balloon.

Figure 17:
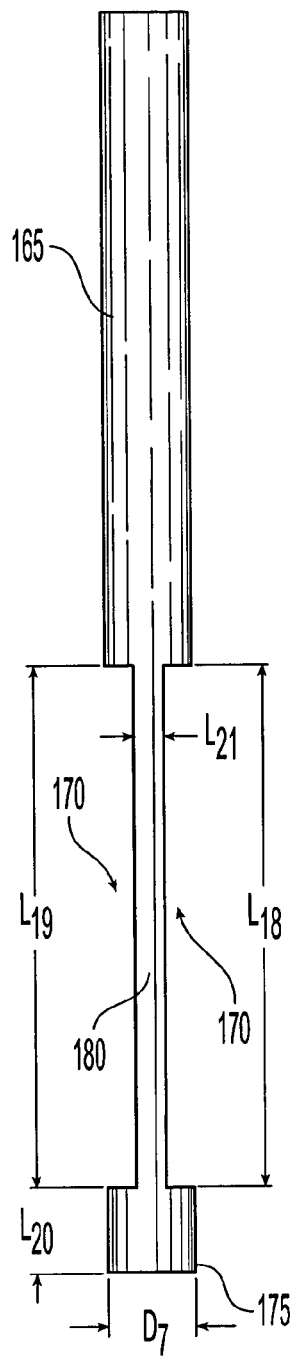
FIG. 17 shows a plan view of the catheter of FIG. 13.
Figure 18:
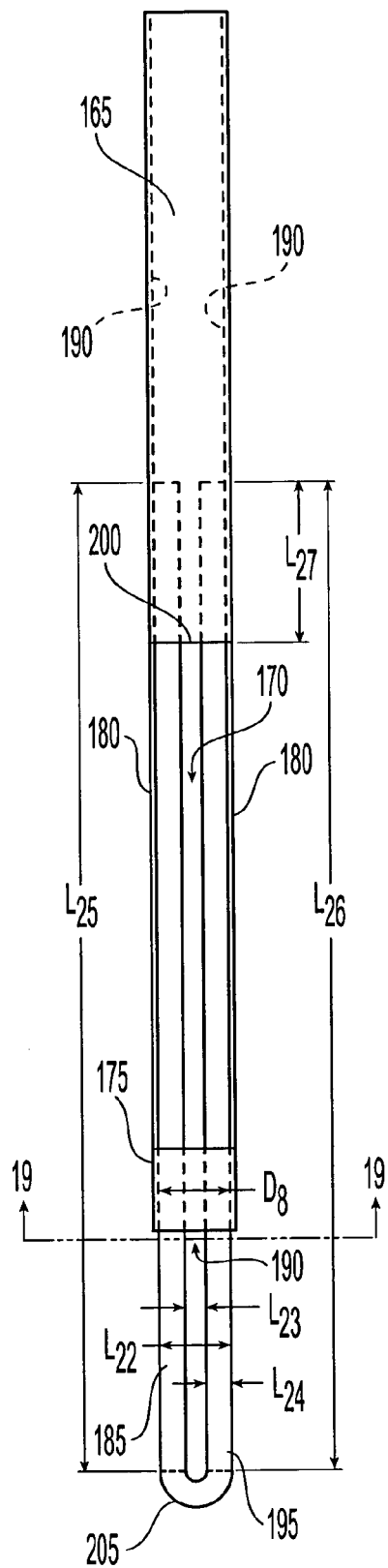
FIG. 18 shows a plan view of an reinforcing insert for the catheter of FIG. 17.
Figure 19:
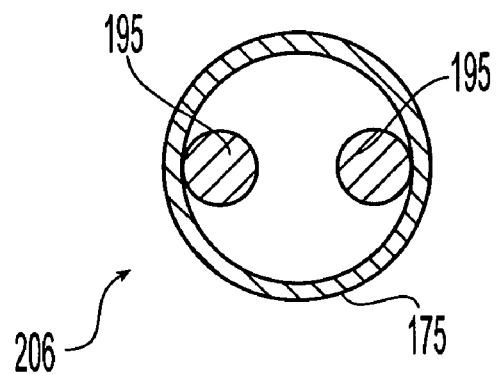
FIG. 19 shows an enlarged sectional view along line 19-19 of FIG. 18.

FIGS. 17-25 depict exemplary embodiments of a catheter construction of the present invention. The basic components of the catheter are shown in FIGS. 17-19. Additional, illustrative embodiments of structural reinforcing elements are presented in FIGS. 20-25. In general the catheter may be constructed with a plurality of openings through which a balloon or plurality of balloons may be deployed. For example, the catheter may have two openings through which a single balloon may be deployed. As the balloon is inflated, the reinforcing members of the catheter that define the openings cause the balloon to expand outwardly away from the catheter. Alternatively, a plurality of balloons may be deployed through the windows either at approximately the same time or in a staged succession. The balloons also may have differing shapes, surface characteristics, or pressures to suit a particular clinical application. The following discussion illustrates non-limiting examples of the present invention using a catheter with windows through which a balloon or balloons are deployed.

FIG. 17 depicts the distal end 175 of the catheter 165 of FIG. 13 in an elevation view. The catheter 165 has an outer diameter D7, a proximal tip length L20, and two circumferentially opposed balloon deployment openings 170. Lengths L18 and L19 of the balloon deployment openings 170, preferably, are the same length. The openings 170, however, may be of different length and size to accommodate a particular balloon. The remaining catheter material 180 between the balloon deployment openings 170 form strips of width L21. Generally, the number of strips 180 correspond to the number of balloon deployment openings 170 provided in the catheter 165. Similarly, the width L21 of each strip 180 may depend on the number of strips 180 provided and the outer diameter D7 of the catheter 165.

FIG. 18 shows the principle structural components of the catheter of FIGS. 17 and 18. The catheter 165 is constructed with inner dimension D8, and an U-rod 185 that is inserted into the catheter 165 via an opening 190 in the distal tip 175. The width L22 of the outer dimension of the U-rod 185 may be sized according to the inner diameter D8, such that the U-rod 185 fits within and bears against the inside wall 190 of the catheter 165. Length L24, the outer dimension of the individual rod 195, is related to the structural reinforcement required for the intermediate catheter strips 180 located between the balloon deployment windows 170. Although, the interior width L23 of the U-rod 185 is related to the geometry of the catheter interior, width L23 is also operably configured to cooperate with the deployed balloon or balloons.

In addition, length L25 and length L26 of the U-rod 185 preferably extend beyond the distal edge 200 of the balloon deployment opening 170 to provide a suitable anchoring length L27 for the U-rod 185 within the catheter 165. U-rod segment lengths L25 and L26 need not be equal. The rounded tip 205 of the U-rod 185 may be fully recessed or may partially extend from the proximal end 175 of the catheter 165. In one embodiment, the tip 205 of the U-rod 185 is secured to the catheter 165 by a soldered, brazed or welded connection. A glued fastener or other attachment means may also be used. For instance, a snap together fastening method may be used. Depending on the number of balloon deployment openings 170 and the material of catheter 165 construction, the number of reinforcing rods 185 will vary. Also, the means for joining a plurality of reinforcing rods 185 together and connecting the reinforcing rods 185 to the catheter 165 may vary from the embodiments shown.

Figure 20:
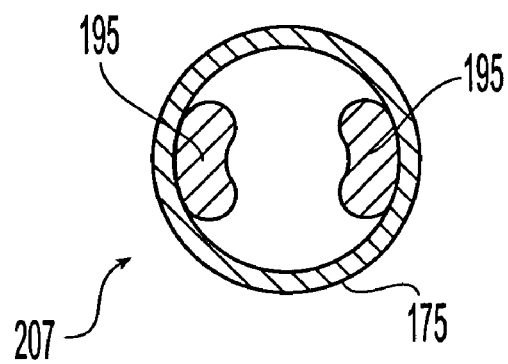
FIG. 20 shows a enlarged sectional view along line 19-19 of another embodiment of the reinforcing insert of FIG. 18.
Figure 21:
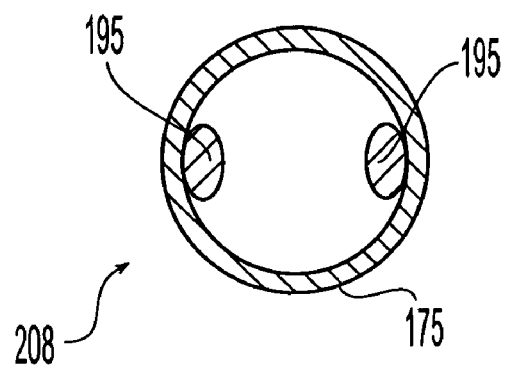
FIG. 21 shows an enlarged sectional view along line 19-19 of another embodiment of the reinforcing insert of FIG. 18.
Figure 22:
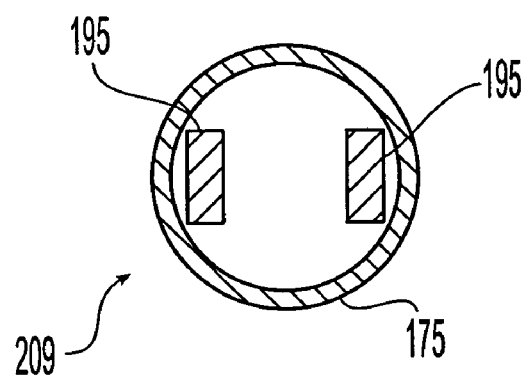
FIG. 22 shows an enlarged sectional view along line 19-19 of another embodiment of the reinforcing insert of FIG. 18.
Figure 23:
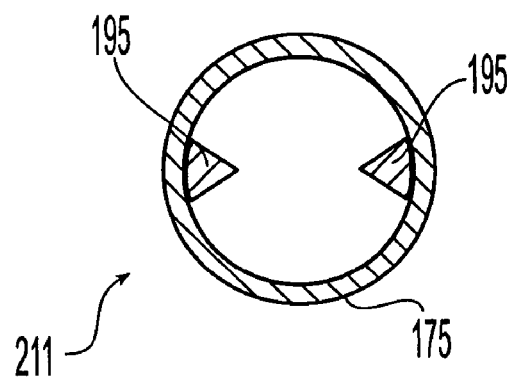
FIG. 23 shows an enlarged sectional view along line 19-19 of another embodiment of the reinforcing insert of FIG. 18.
Figure 24:
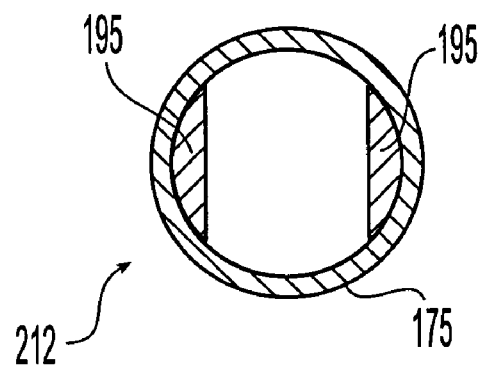
FIG. 24 shows an enlarged sectional view along line 19-19 of another embodiment of the reinforcing insert of FIG. 18.

FIG. 19 is a sectional view through line 19-19 of FIG. 18 and shows individual reinforcing rods 195 with an exemplary cross section. In this illustrative embodiment, reinforcing rod 206 is circular in cross-section. As one skilled in the art would appreciate, the geometry of the reinforcing rod may be selected to provide a beneficial combination of clearance and strength. For instance, FIGS. 20-25 depict individual reinforcing rods 195 with other illustrative geometric cross sections. The reinforcing rod of FIG. 20 shows an embodiment with kidney bean shaped cross-section. FIG. 21 shows a reinforcing rod with oval shaped cross-section. FIGS. 22 and 23 show reinforcing rod embodiments with rectangular and triangular shaped cross-sections, respectively. FIG. 24, by contrast, shows an exemplary reinforcing rod with a circular section shaped cross-section.

In addition, multiple rods may be used instead of a U-rod to accommodate a reinforced catheter with a plurality of balloon deployment openings. One skilled in the art would readily appreciate that one particular geometry of reinforcing rods may prove easiest to manufacture, assemble, or configure. Therefore, one embodiment may prove to be the most cost effective solution for a particular balloon configuration. For this reason, these embodiments are not intended to be a complete set of cross sections contemplated by the invention, rather general illustrations of the reinforcing rod concept. TABLE 4 presents general dimensions for the catheter depicted in FIGS. 17-18. Values presented in range 1 represent generally preferred dimensions and characteristics. Values presented in range 2, by comparison, represent more preferred criteria.

TABLE 4

PREFERRED EMBODIMENTS FOR WINDOWED CATHETERS

| Target Bone Anatomy | Preferred Size | D7 (a) (mm) | D8 (b) (mm) | L18, L19 (mm) | L20 (mm) | L21 (mm) | L22 (mm) | L23 (mm) | L24 (mm) | L25 L26 (mm) |
|---|---|---|---|---|---|---|---|---|---|---|
| Vertebral Body | Range 1 | 2-7 | 1.5-6.9 | 10-35 | 0.25-10 | 0.2-4 | 0.5-6.9 | 0.5-6.5 | 0.2-3 | 10.5-50 |
|  | Range 2 | 3-5 | 2.5-4.9 | 15-25 | 2-6 | 0.5-2.5 | 2-4.9 | 1.5-4 | 0.5-1.75 | 18-35 |
| Distal Radius | Range 1 | 2-7 | 1.5-6.9 | 10-45 | 0.25-10 | 0.2-4 | 0.5-6.9 | 0.5-6.5 | 0.2-3 | 10.5-65 |
|  | Range 2 | 3-5 | 2.5-4.9 | 15-25 | 2-6 | 0.5-2.5 | 2-4.9 | 1.5-4 | 0.5-1.75 | 18-35 |
| Calcaneus | Range 1 | 2-7 | 1.5-6.9 | 5-35 | 0.25-10 | 0.2-4 | 0.5-6.9 | 0.5-6.5 | 0.2-3 | 5.5-50 |
|  | Range 2 | 3-5 | 2.5-4.9 | 12-28 | 2-6 | 0.5-2.5 | 2-4.9 | 1.5-4 | 0.5-1.75 | 15-35 |

TABLE 4-continued

PREFERRED EMBODIMENTS FOR WINDOWED CATHETERS

| Target Bone Anatomy | Preferred Size | D7 (a) (mm) | D8 (b) (mm) | L18, L19 (mm) | L20 (mm) | L21 (mm) | L22 (mm) | L23 (mm) | L24 (mm) | L25 L26 (mm) |
|---|---|---|---|---|---|---|---|---|---|---|
| Tibial Plateau | Range 1 | 2-9 | 1.5-8.9 | 15-60 | 0.25-10 | 0.2-6.5 | 0.5-8.9 | 0.5-8.5 | 0.2-4 | 13.5-80 |
|  | Range 2 | 3-7 | 2.5-6.8 | 20-40 | 2-6 | 0.5-4 | 2-6.8 | 1.5-6 | 0.5-2.5 | 18-50 |

(a) Outer Diameter
(b) Inner Diameter

Reinforcing elements, alternatively, may be individual rails which are connected to and oriented around the catheter perimeter by a plurality of spacer rings which are mounted on an internal lumen. The reinforcing elements may further be wire elements that are post tensioned at the distal tip of the catheter. For this reason, the relative sizing of the balloon deployment window, the catheter strips and the reinforcing elements may be reconfigured to accommodate a particular anatomical, mechanical, therapeutic, or clinical need.

Figure 25:
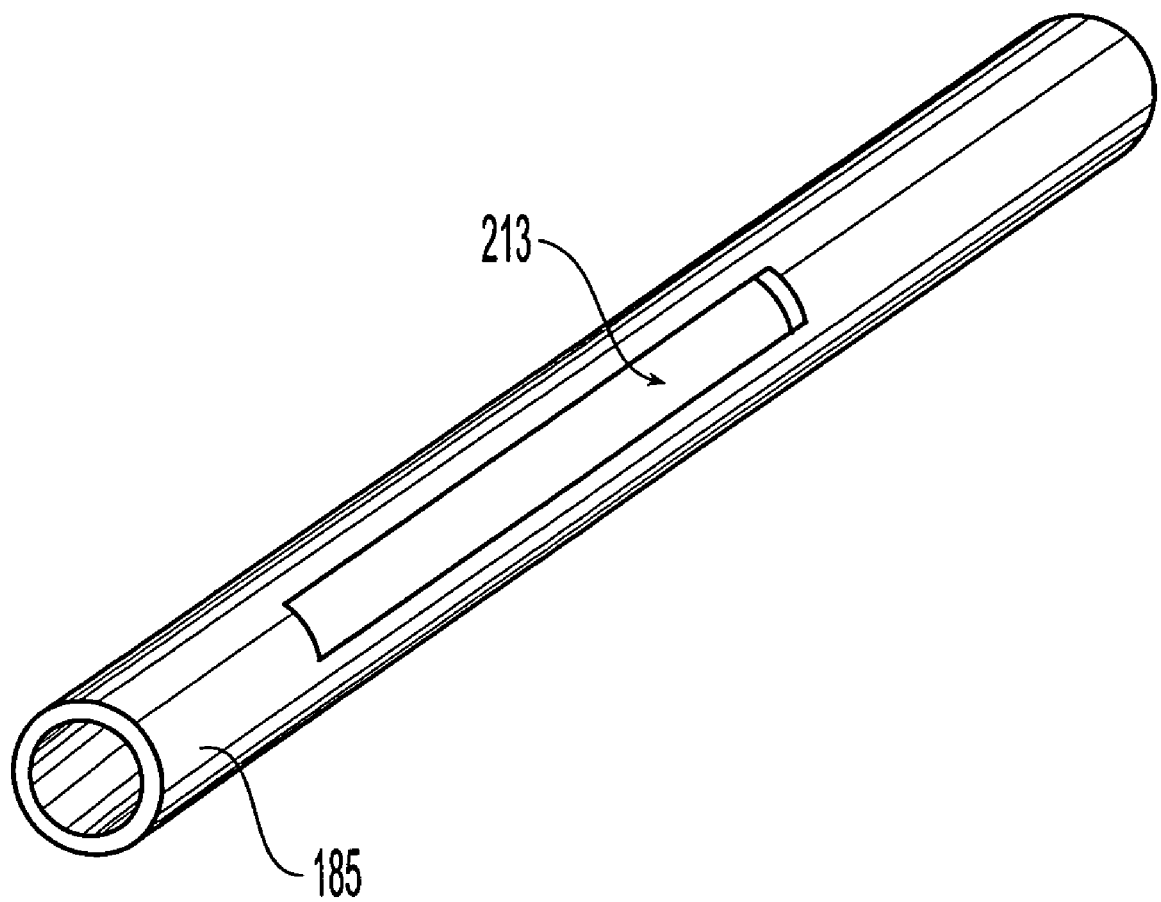
FIG. 25 shows a perspective view of an exemplary embodiment of a reinforcing insert for the catheter of FIG. 17.

For example, FIG. 25 shows an alternative reinforcing structure to the rods depicted in FIGS. 17-24. The reinforcing member of FIG. 25 may be tubular in construction and provided with a slot 213 for deploying one or more inflatable devices. The tubular reinforcing element may formed by a special extrusion that provides, for example, thicker (i.e., stronger) walls in selected locations. As one skilled in the art would appreciate, a tubular catheter reinforcing member may require more than one slot to accommodate a device with a plurality of balloon deployment windows. Additionally, more than one balloon may be deployed through each deployment window. Thus, in one embodiment, a single balloon with a plurality of chambers may be deployed through one deployment window. In another embodiment, two separate balloons may be deployed through a single deployment opening. In yet another embodiment, a single balloon with a plurality of chambers may be deployed through an equal number of balloon deployment openings.

FIGS. 26-35, show illustrative complex balloon embodiments constructed from the balloons described in the fore going figures and tables.

Figure 26:
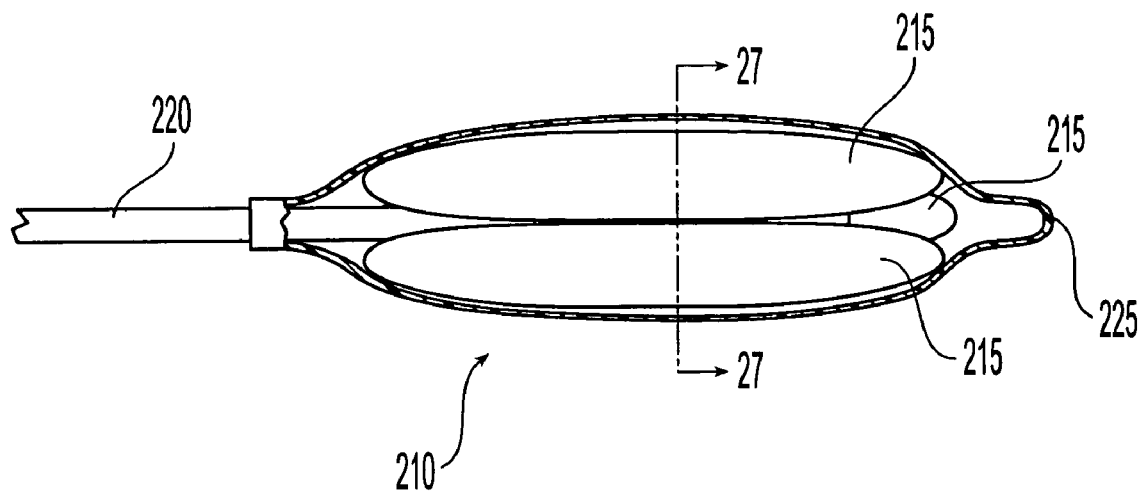
FIG. 26 shows a partial sectional view along the longitudinal axis of another embodiment of the balloon catheter of FIG. 1.
Figure 27:
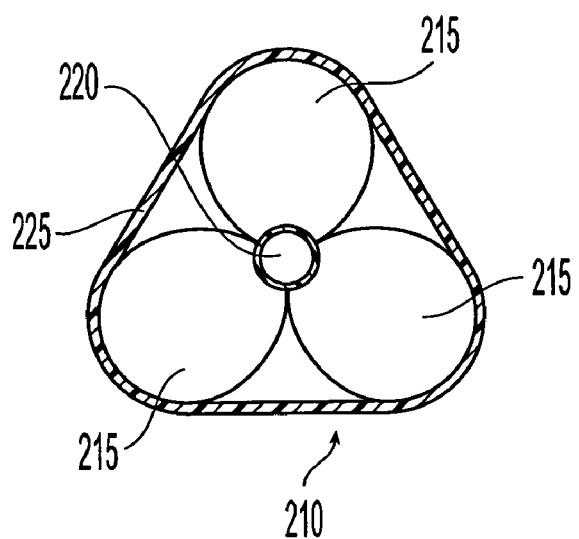
FIG. 27 shows a sectional view through line 27-27 of FIG. 26

FIGS. 26 and 27 show a balloon catheter with three balloons and three deployment windows. The complex balloon 210 comprises three offset circular balloons 215 stemming from a central catheter 220 and enclosed by an optional outer layer 225. In one embodiment, the individual balloons 215 are comprised of single layers. In another embodiment, the individual balloons may be formed from a plurality of layers and materials. Alternatively, in another embodiment, the complex balloon may comprise a single balloon with three chambers enclosed by an optional outer layer 225. One skilled in the art would readily appreciate that the thickness of each of these layers may be different, and that complex balloons may achieve large effective outer diameters, with thinner balloon walls. Thus, a complex balloon may provide surprising benefits and high levels of clinical performance including: increased resistance to puncture and tearing, novel positioning abilities, enhanced deployment, improved retractability, and ease of removal.

Figure 28:
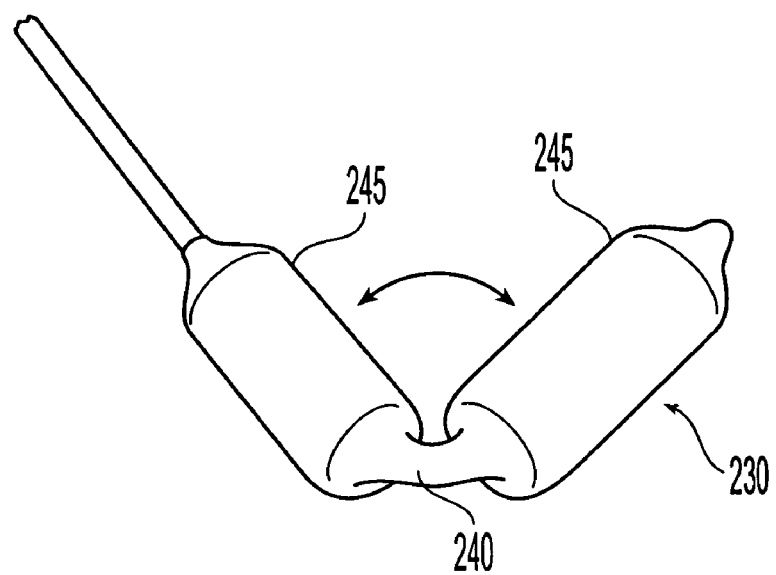
FIG. 28 shows a perspective view of another embodiment of the balloon of FIG. 1.
Figure 29:
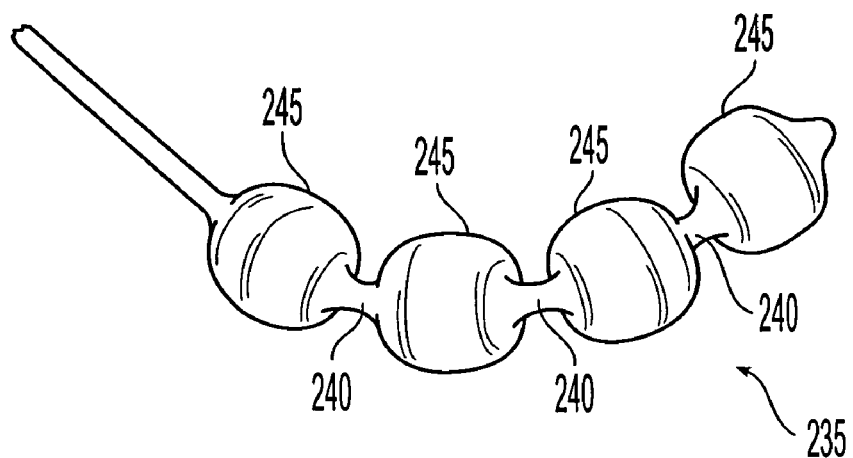
FIG. 29 shows a perspective view of another embodiment of the balloon of FIG. 1.
Figure 30:
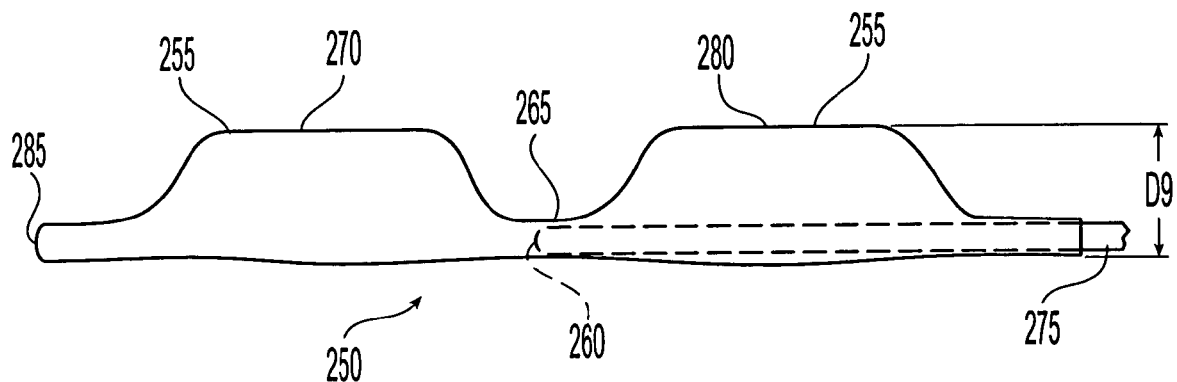
FIG. 30 shows an intermediate perspective view of another embodiment of the balloon of FIG. 1.
Figure 31:
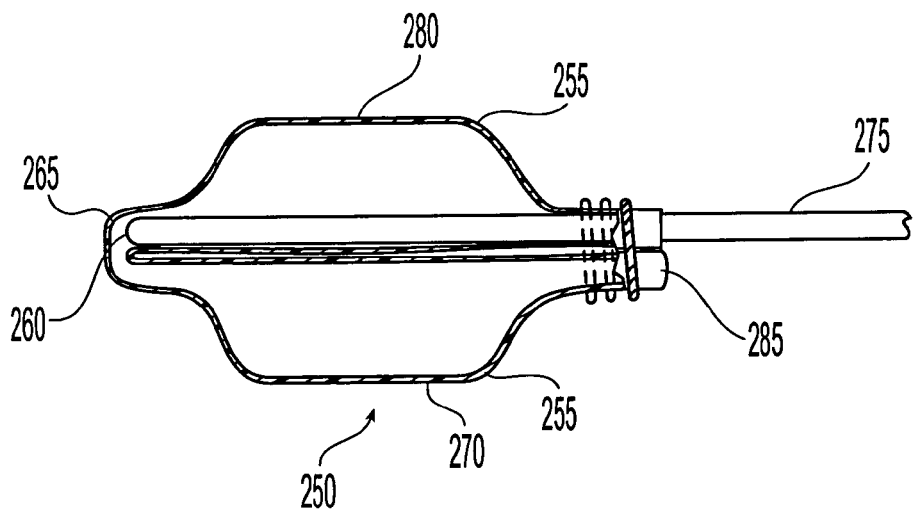
FIG. 31 shows a partial sectional view along the longitudinal axis of the fully constructed balloon of FIG. 30.

FIGS. 28 and 29, depict axial balloon embodiments 230 and 235 having uniform diameter and at least one integral hinge 240, which separates the working length of the balloon into a plurality of segments. Adjacent balloon segments are free to move about the common hinge. FIG. 30, by contrast, represents an offset balloon 250 with two large chambers 255 connected in serial. In one embodiment, a catheter tip 260 is inserted into the balloon 250 to a point 265 about equidistant from the balloon chambers 255. Referring to FIG. 31, the second chamber 270 of the balloon 250 is then folded over the tip 260 and doubled back along the length of the catheter 275. Further, the folded over portion 270 of the balloon 255 may be secured to the non-folded portion 280 and tied to the catheter 275 near the proximal end of the balloon. In another embodiment, the doubled chambered balloon is constructed of two layers. In yet another embodiment, an inner balloon is folded about the catheter and then the entire composite structure is then wrapped within an additional outer layer. In one embodiment, the outer diameter D9 of the balloon 250 ranges from 2 mm to 12 mm.

Figure 32:
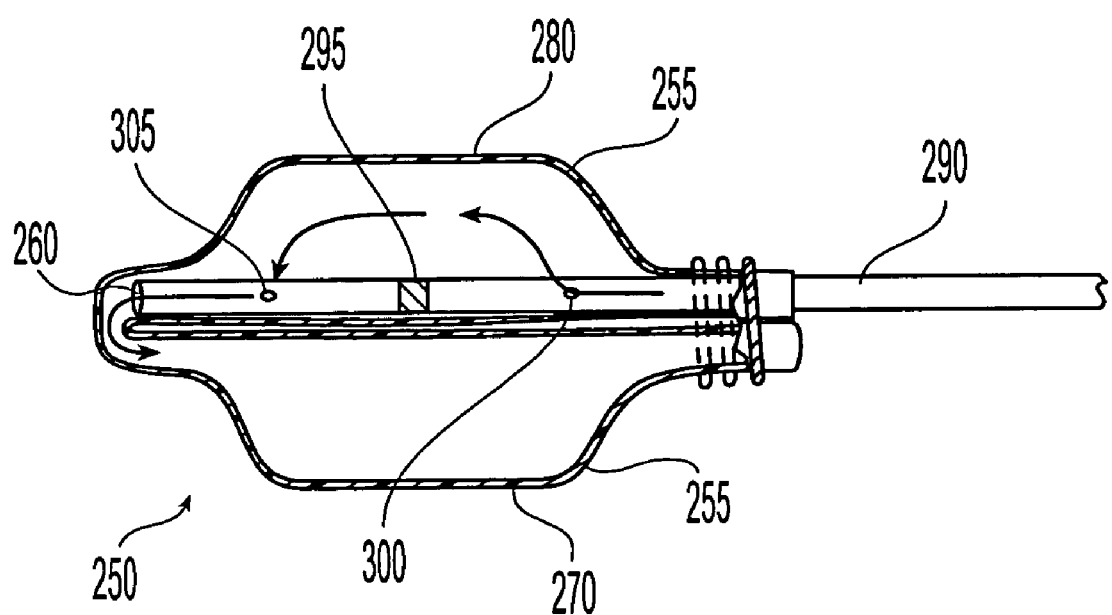
FIG. 32 shows a schematic representation of the catheter construction of the balloon of FIG. 30.

In yet another embodiment, shown in FIG. 32, a specially constructed catheter 290 may be used to provide fluid to the balloon chambers 255 in a sequential manner. During balloon inflation, fluid is prevented from being transported directly into the second chamber 270 of the balloon 250, by a closed valve or blockage 295 in the catheter. The inflation fluid is directed into the first chamber 280 of the balloon 250 via an aperture 300 located on the distal side of the blockage 295 in the catheter 290. The fluid partially fills the first balloon chamber 280, and then renters the catheter 290 via an additional aperture 305 located on the proximal side of the blockage 295 in the catheter 290. As the fluid continues to fill the first chamber 280 of the balloon 250, fluid also starts to migrate through the proximal end of the blocked catheter 290 to the second balloon chamber 270 via an opening in the tip 260 of the catheter 290.

As shown further in FIG. 32, the proximal tip 260 of the catheter 290 provides a fluid connection between the first 280 and second 270 balloon chambers 255. When the balloon 250 is deflated, the direction of fluid transport is reversed. In one embodiment, the blockage 295 in the catheter 290 is removed to allow fluid flow throughout the length of the catheter 290. In another embodiment, a pressure activated valve, opens to permit free fluid flow through the catheter, when the pressure in the second chamber 270 of the balloon 250 becomes larger than a predetermined pressure in the first balloon chamber 280. In yet another embodiment, the catheter blockage 295 may be selectively controlled by the surgeon and formed from a shape memory metal, that would provide by-pass flow in one state, and direct catheter flow in a second state.

One skilled in the art would readily appreciate that more apertures may be used as appropriate to effect the desired rate of fluid transfer, and that a folded multi-chamber balloon may be simple to assemble and test during manufacturing. Thus, creating complex balloons from a folded multi-chamber balloon 250 embodiments may also provide cost savings.

Figure 33:
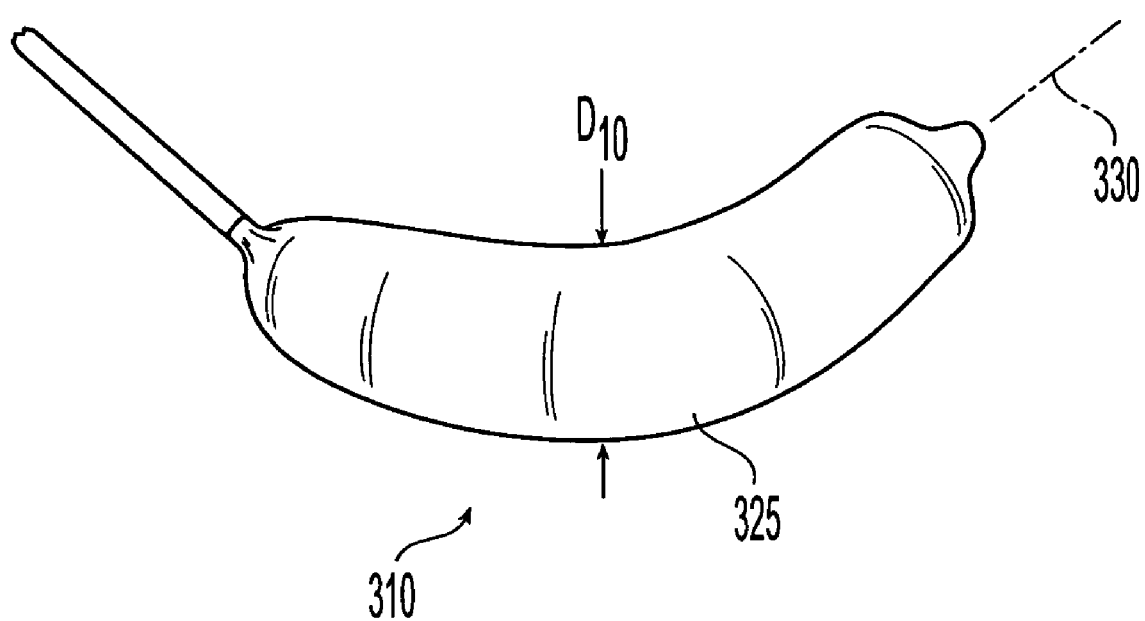
FIG. 33 shows a perspective view of another embodiment of the balloon of FIG. 1.
Figure 34:
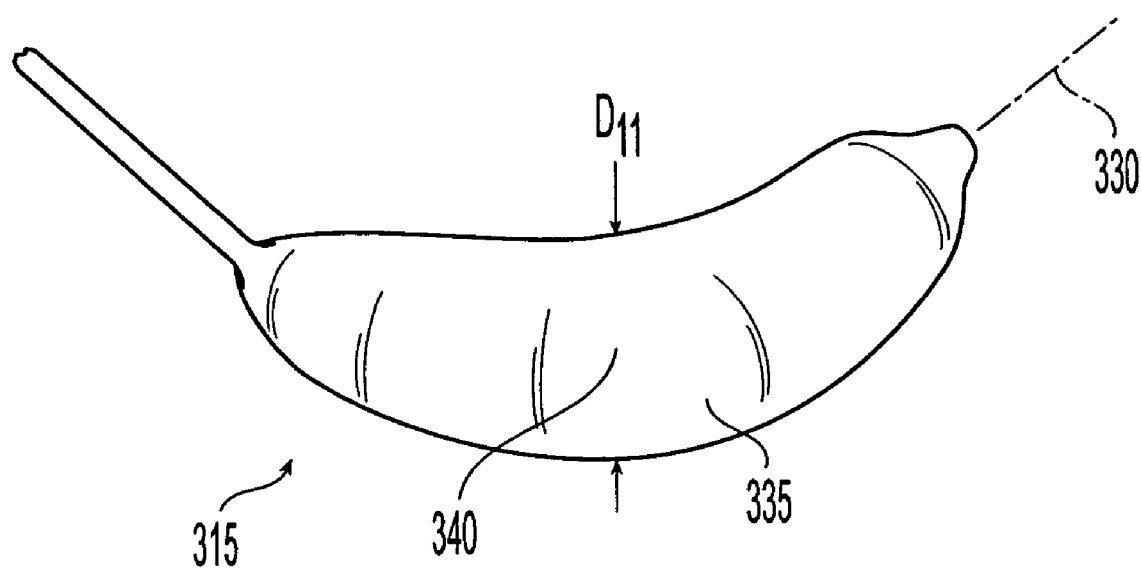
FIG. 34 shows a perspective view of another embodiment of the balloon of FIG. 1.
Figure 35:
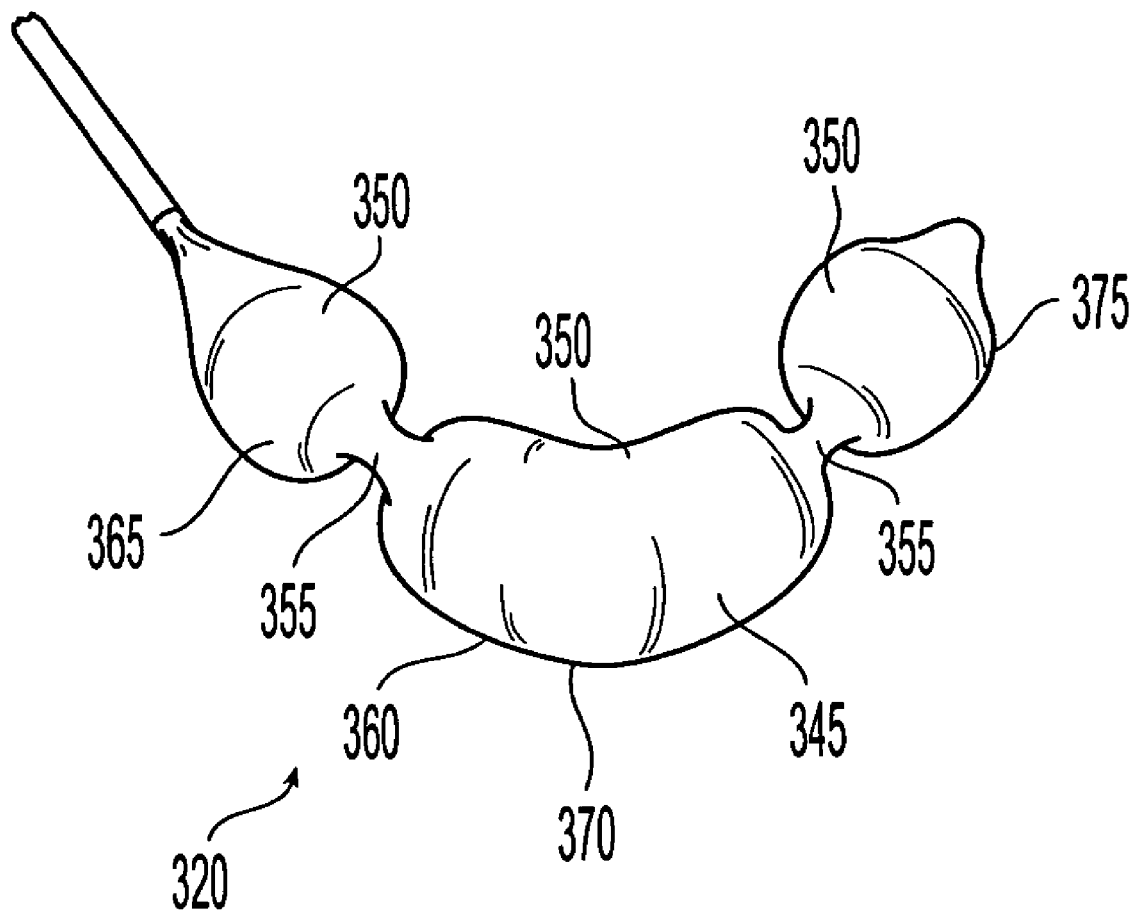
FIG. 35 shows a perspective view of another embodiment of the balloon of FIG. 1.

Similarly, FIGS. 33-35 depict additional exemplary balloon embodiments 310, 315, and 320. FIG. 33, for example, depicts an axially offset balloon 325 with a uniform diameter D10 and curved shape. In one embodiment, the curved balloon 325 having longitudinal axis 330 may intimately contact the walls of the prepared bone cavity. Alignment of balloon-applied forces with the bone damage facilitates a shape appropriate restoration of the bone anatomy. In another embodiment, the curve is provided by a curved catheter or a catheter made from shape memory metal, rather, than molding the shape into the balloon. In another embodiment, the curved balloon is formed from an axially offset balloon 335 having non uniform diameter. For example, the balloon of FIG. 34 has a diameter that varies along the longitudinal axis of the balloon. In the illustrative embodiment shown in FIG. 34, the largest diameter D11 is located at the longitudinal 330 midpoint 340 of the balloon 335. In yet another embodiment, shown in FIG. 35, the balloon 320 has three chambers 350, two hinges 355, and a curved central section 365. In another embodiment of the balloon of FIG. 35, the structure of the balloon 320 allows for the controlled inflation and deflation of the individual chambers 365, 370, and 375.

Figure 36:
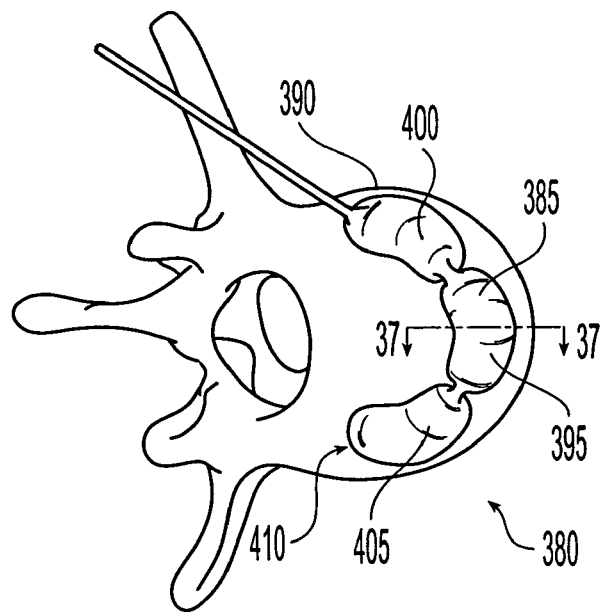
FIG. 36 shows a plan view of another embodiment of the balloon catheter of FIG. 1.

FIG. 36 depicts a sectional view through the longitudinal axis of the spine, and shows a multi-chambered and hinged balloon 385 within a vertebral bone 390. In this embodiment the complex balloon has the advantage of allowing selected chambers (e.g., chamber 395) to be deflated first before the other sections (e.g. chambers 400 and 405). Thus, cavity 410 could then be partially filled with bone cement without deflating or removing the outer balloon chambers 400 and 405 and the restored anatomy of the bone 390 could be fully or nearly fully maintained during the transition from bone fracture reduction to bone fixation. In another embodiment, bone filling material can be applied to the cavity as the balloon sections are deflated. In yet another series of embodiments, the multiple balloon chambers of FIGS. 35-37 may be formed from shared septum membranes, rather, than narrowed passageways or hinges.

Figure 37:
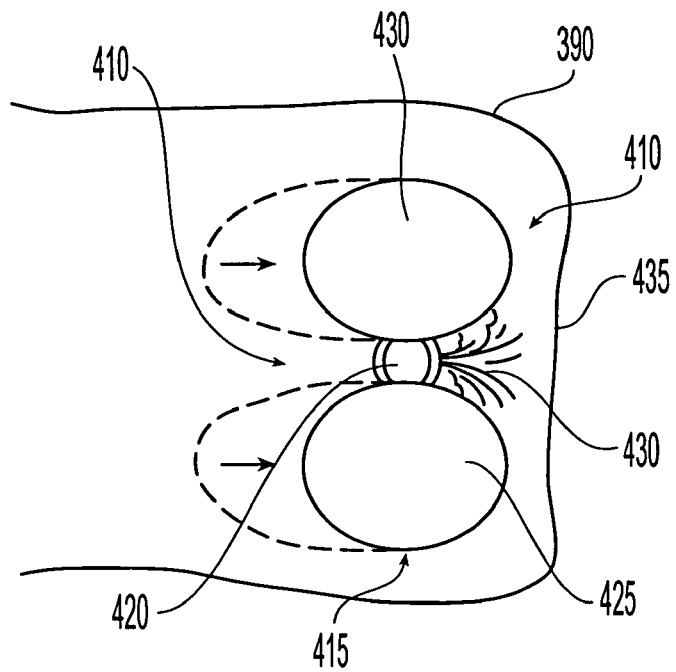
FIG. 37 shows a sectional view through line 37-37 of FIG. 36.

FIG. 37 which is taken along line 37-37 of FIG. 36, depicts a central catheter 420 with offset circular balloons 425 and 430. As the top 430 and bottom 425 balloon are deflated, bone cement 430 is filled against the outer wall 435 of the cavity 410 in the restored vertebrae 390. In this fashion, a controlled volume exchange between the inflated structure 430 and 425 and the bone filling material 430 is accomplished. Thus, multiple-chambered balloons offer the potential for surprising advantages, such as controlled volume exchange between the restorative balloon and the bone filling material. Similarly, one skilled in the art would also readily appreciate that multi-chamber balloons may also be used for sequential filling of restored bone cavities. For example, the inflated structure in a stronger part of the bone may be deflated while balloons supporting weaker portions of the bone remain deployed. The region of the bone where the balloon is deflated may then be filled with bone filler material and allowed to harden or gel. Then, neighboring or other balloons may be selectively deflated and the regions filled in a similar manner. In this manner, controlled deflation of a multi-chambered balloon provides temporary support to selected areas of the restored bone anatomy while other areas are filled with bone filler material.

While the above invention has been described with reference to certain preferred embodiments, it should be kept in mind that the scope of the present invention is not limited to these embodiments. The balloon can be modified or extended to accommodate particular formulations of balloon construction materials or fabrication techniques which may require multiple layers with different relative locations one to another (e.g., placing one layer on the outside and a second layer on the inside.) Similarly, the number and spacing of the balloon openings in the catheter and the reinforcing method may be changed to better implement the window deployment of one or more inflatable structures. Also, balloons with dimple forming projections may be produced to the extent they do not impede significantly ultimate balloon performance. Different balloon materials and surface coatings, or outer layers of different materials or surface coatings may also be applied to the balloon to facilitate a smaller balloon profile. The embodiments above can also be modified so that some features of one embodiment are used with the features of another embodiment. One skilled in the art may find variations of these preferred embodiments which, nevertheless, fall within the spirit of the present invention, whose scope is defined by the claims set forth below.

What is claimed is:

1. An inflatable device for treating bone comprising a first component forming a barrier configured and adapted for insertion into bone, the barrier having a proximal end and a distal end, a longitudinal axis and inner and outer surfaces, the proximal end of the barrier being secured to a distal end of a catheter and the distal end of the barrier, upon inflation, extending away from the distal end of the catheter such that the longitudinal axis of the barrier is substantially parallel to a longitudinal axis of the catheter, the inner surface defining an enclosure having a port to receive filler material, the outer surface configured to contact and substantially conform to the surface of the bone, the barrier having an insertion configuration for placement in a bone cavity and an expanded configuration providing the enclosure to receive the filler material without releasing the filler material into the bone cavity;

wherein the barrier includes at least one rupture site configured to fail under a triggering condition, such that the expanded configuration of the barrier has a first condition which contains the filler material within the enclosure and a second condition which releases the filler material from the enclosure upon failure of the at least one rupture site due to the triggering condition;

wherein the at least one rupture site includes a plurality predetermined seams configured to fail under the triggering condition, the plurality of predetermined seams running parallel to the longitudinal axis of the barrier and originating from the distal end of the barrier and ending at the proximal end of the barrier, and the predetermined seams configured to fail so that, after the triggering condition has occurred, the barrier resembles an open banana peel; and wherein at least one of the plurality of predetermined seams are resorbable.

2. The inflatable device of claim 1, wherein the device comprises a second component and the second component is a woven braid.

3. The inflatable device of claim 2, wherein the woven braid forms a predetermined shape.

4. The inflatable device of claim 1, wherein the first component comprises an essentially inelastic material.

5. The inflatable device of claim 1, wherein the first component comprises an essentially semi-elastic material.

6. The inflatable device of claim 1, wherein the first component comprises an essentially elastic material.

7. The inflatable device of claim 2, wherein the second component comprises an essentially inelastic material.

8. The inflatable device of claim 1, further comprising a medicament.

9. The inflatable device of claim 8, wherein the medicament is disposed on an outer surface of the barrier.

10. The inflatable device of claim 8, wherein the medicament is disposed on an inner surface of the barrier.

11. The inflatable device of claim 2, wherein the second component is at least partially resorbable.

12. The inflatable device of claim 1, wherein the first component is at least partially resorbable.

13. The inflatable device of claim 12, wherein the device comprises a second component that is at least partially resorbable.

14. The inflatable device of claim 12, wherein the first component further comprises a medicament that can be released as the first component is resorbed.

15. The inflatable device of claim 1, further comprising a coating on the outer surface of the first component.

16. The inflatable device of claim 15, wherein the coating comprises a layer of hydrophobic material.

17. The inflatable device of claim 15, wherein the coating comprises a layer of hydrophilic material.

18. The inflatable device of claim 15, wherein the coating comprises a layer of material having a high friction surface.

19. The inflatable device of claim 15, wherein the coating comprises a layer of material having a low friction surface.

20. The inflatable device of claim 15, wherein the coating is resorbable.

21. The inflatable device of claim 15, wherein the coating covers essentially all of the outer surface of the first component.

22. The inflatable device of claim 1, wherein the first component is perforated.

23. The inflatable device of claim 1, wherein the triggering condition comprises a chemical concentration proximate to one of the inner and outer surfaces of the barrier.

24. The inflatable device of claim 1, wherein the one or more predetermined seams define a region of the barrier.

25. A device for containing material inside bone comprising:
   a barrier member configured and adapted for insertion into bone, the barrier member having a proximal end and a distal end, a longitudinal axis and inner and outer surfaces, the proximal end of the barrier being secured to a distal end of a catheter and the distal end of the barrier, upon inflation, extending away from the distal end of the catheter such that the longitudinal axis of the barrier is substantially parallel to a longitudinal axis of the catheter, with the inner surface defining a space, the barrier having an insertion configuration for placement in a bone cavity and an expanded configuration providing the space to receive filler material without releasing the filler material into the bone cavity;
   wherein the barrier includes at least one rupture site configured to fail under a triggering condition; and
   wherein in a first configuration of the expanded configuration the barrier member prevents material within the space from passing through the inner surface to the outer surface, and in a second configuration of the expanded configuration the barrier member opens to release material from within the space to the outer surface of the barrier member upon failure of the at least one rupture site due to the triggering condition;
   wherein the at least one rupture site includes a single predetermined seam configured to fail under the triggering condition, the predetermined seam originating at a distal end of the barrier and having a generally spiral configuration about the longitudinal axis of the barrier so that, after the triggering condition has occurred, the barrier resembles an orange peel; and
   wherein the predetermined seam is resorbable.

26. The device of claim 25, wherein the predetermined seam is configured and adapted to open when the triggering condition occurs.

27. The device of claim 26, wherein the triggering condition comprises a chemical concentration proximate the inner surface of the barrier member.

28. The device of claim 26, wherein the triggering condition comprises a chemical concentration proximate the outer surface of the barrier member.

29. The device of claim 25, wherein each rupture site is pressure-sensitive.

30. A device for containing material inside bone comprising:
   a flexible member configured and adapted for insertion into bone, the flexible member having a proximal end and a distal end, inner and outer surfaces, a longitudinal axis and a plurality of predetermined seams, with the inner surface defining a substantially enclosed space, the proximal end of the barrier being secured to a distal end of a catheter and the distal end of the barrier, upon inflation, extending away from the distal end of the catheter such that the longitudinal axis of the barrier is substantially parallel to a longitudinal axis of the catheter; and
   a flowable substance disposed in the space;
   wherein the flexible member is expanded under pressure to reduce a fracture in bone and wherein in a first configuration the flexible member resists migration of the flowable material through the inner surface, and in a second configuration the flexible member opens to release material through the inner surface to the outer surface of the flexible member upon rupturing of the seam under a triggering condition;
   wherein the plurality of predetermined seams run parallel to the longitudinal axis of the flexible member and originate from the distal end of the flexible member and end at the proximal end of the flexible member, and the predetermined seams configured to fail so that, after the triggering condition has occurred, the barrier resembles an open banana peel; and
   wherein at least one of the plurality of predetermined seams are resorbable.

31. The device of claim 30, wherein at least one of the plurality of predetermined seams are pressure-sensitive.

32. The device of claim 30, wherein at least one of the plurality of predetermined seams are chemical-sensitive.

* * * * *